United States Patent
Ruan et al.

(10) Patent No.: US 12,318,504 B2
(45) Date of Patent: *Jun. 3, 2025

(54) METHOD FOR MANUFACTURING A CALCIFIED TISSUE SUBSTITUTE

(71) Applicant: Marine Biomedical Pty Ltd, Perth (AU)

(72) Inventors: Rui Ruan, Nedlands (AU); Ming-Hao Zheng, City Beach (AU)

(73) Assignee: Marine Biomedical Pty Ltd, Perth (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/454,753

(22) Filed: Aug. 23, 2023

(65) Prior Publication Data
US 2023/0390455 A1 Dec. 7, 2023

Related U.S. Application Data

(63) Continuation of application No. 16/618,684, filed as application No. PCT/AU2018/050541 on Jun. 1, 2018, now Pat. No. 11,771,800.

(30) Foreign Application Priority Data

Jun. 2, 2017 (AU) .......................... AU2017902108

(51) Int. Cl.
| | |
|---|---|
| A61L 27/12 | (2006.01) |
| A61K 33/06 | (2006.01) |
| A61K 33/42 | (2006.01) |
| A61L 27/36 | (2006.01) |

(52) U.S. Cl.
CPC .............. *A61L 27/12* (2013.01); *A61K 33/06* (2013.01); *A61K 33/42* (2013.01); *A61L 27/3604* (2013.01); *A61L 2400/06* (2013.01); *A61L 2430/02* (2013.01); *A61L 2430/12* (2013.01)

(58) Field of Classification Search
CPC .................................................. A61L 2430/02
See application file for complete search history.

(56) References Cited

U.S. PATENT DOCUMENTS

| | | | |
|---|---|---|---|
| 5,755,787 A | 5/1998 | Camprasse | |
| 6,905,516 B1 * | 6/2005 | Lemaitre | A61F 2/28 623/23.62 |
| 9,642,939 B2 * | 5/2017 | Khairoun | A61L 24/0042 |
| 10,342,897 B2 * | 7/2019 | Altschuler | A61L 27/3834 |
| 2006/0233849 A1 * | 10/2006 | Simon | A61L 24/0042 424/422 |
| 2010/0068243 A1 * | 3/2010 | Khairoun | A61L 27/56 424/600 |
| 2010/0154681 A1 | 6/2010 | Yeh | |
| 2012/0207839 A1 | 8/2012 | Liu | |
| 2015/0147397 A1 | 5/2015 | Altschuler | |

FOREIGN PATENT DOCUMENTS

WO WO 2009/029734 A2 3/2009

OTHER PUBLICATIONS

Ming Ni et al, Nacre surface transformation to hydroxyapatite in a phosphate buffer solution, Biomaterials 24 (2003) 4323-4331, publication date: 2003 (Year: 2003).*
The International Search Report for International Application No. PCT/AU2018/050541; mailed Aug. 15, 2018, three pages.
Combes et al. "Calcium carbonate-calcium phosphate mixed cement compositions for bone reconstruction" J. Biomed. Mater. Res. (2006) vol. 79A (2), pp. 318-332.
Fontaine et al. "New calcium carbonate-based cements for bone reconstruction" Key Engineering Materials (2005) vol. 284-286, pp. 105-108.
Gerhard et al. "Design strategies and applications of nacre-based biomaterials" Acta Biomaterialia (2017) vol. 54, pp. 21-34, available online Mar. 6, 2017.
Kon et al. "Strengthening of calcium phosphate cement by compounding calcium carbonate whiskers" Dental Materials Journal (2005) vol. 24 no. 1, pp. 104-110.
Ni & Ratner, "Nacre surface transformation to hydroxyapatite in a phosphate buffer solution" Biomaterials (2003) vol. 24, pp. 4323-4331.
Zhang et al. "Nacre, a natural, multi-use, and timely biomaterial for bone graft substitution" J. Biomed. Mater. Res. Part A (2017) vol. 105A, pp. 662-671, published online Nov. 7, 2016.
The Extended European Search Report (EESR) for corresponding European patentapplication No. 18810375.8. dated Jan. 18, 2021, pp. 1-8.
Ming Ni and Buddy Ratner, "Nacre surface transformation to hydroxyapatite in a phosphate buffer solution", Biomaterials, 24, p. 4323-4331 (2003).
Yaping Guo, Transformation of nacre coatings into apatite coatings ni phosphate buffer solution at low temperature, Journal of Biomedical Materials Research, Published online Nov. 9, 2007 in Wiley InterScience (Year: 2007).

(Continued)

*Primary Examiner* — Mark V Stevens
*Assistant Examiner* — Alparslan Asan
(74) *Attorney, Agent, or Firm* — McDonnell Boehnen Hulbert & Berghoff LLP

(57) ABSTRACT

The invention relates to a method for manufacturing a calcified tissue substitute, the method comprising: reacting ground nacre, monocalcium phosphate, and water to produce brushite; grinding the brushite; reacting ground nacre with the ground brushite in disodium hydrogenphosphate solution. The invention also relates to a calcified tissue substitute manufactured by the method, use of the calcified tissue substitute for repairing a calcified tissue, and a delivery device for delivering the calcified tissue.

15 Claims, 20 Drawing Sheets

(56) References Cited

OTHER PUBLICATIONS

Springer, Annexure: Buffers, Solutions and Miscellaneous Procedures, downloaded ni Dec. 2021 (Year: 2021).
Gabriela A. Farfan, Mineralogy of Deep-Sea Coral Aragonites as a Function of AragoniteSaturation State, Frontiers in Marine Science, publication date: Dec. 10, 2018 (Year: 2018).

* cited by examiner

D

Surgery Control

A defect of 5mm in diameter with depth of the full thickness of cortical bone

Surgery Control

A 2 mm defect from the *linea epiphysialis* was created in the cortical bone diaphysis

C

METHOD FOR MANUFACTURING A CALCIFIED TISSUE SUBSTITUTE

This application is a continuation of U.S. application Ser. No. 16/618,684, filed Dec. 2, 2019, which is a U.S. National Stage under 35 U.S.C. § 371 of International Application No. PCT/AU2018/050541, filed Jun. 1, 2018, which claims the benefit of Australian Application No. AU 2017902108, filed Jun. 2, 2017, all of which are incorporated by reference herein in their entirety.

FIELD

The present invention relates to manufacture of a calcified tissue substitute.

BACKGROUND

Defects caused by infection, trauma, inflammation and tumorous and congenital aetiologies are the most common orthopaedic and dental conditions that require extensive surgical treatment. A number of bone substitutes have been developed as medical devices used in the injectable and implantable forms, but the majority of them lack sufficient osteoconductivity and osteoinductivity. In spite of this, bone substitutes have an extensive clinical application in the orthopaedic and dental fields with a market value of over $8 billion per year.

Nacre has been shown to induce bone healing, which can be traced back to the era of the Maya. It has been documented that nacre and pearls contain trace elements and bioactive proteins that can induce bone formation. However, the rapid degradation rate of the calcium carbonate in nacre has limited its application as an implantable or injectable bone substitute.

Accordingly, there is a need for an improved composition for repairing a calcified tissue.

Generation of porous materials for repairing a calcified tissue is an essential design criterion for improvement of material composition. Currently there are two main porous materials—prefabricated porous materials and a porous material whose porous structure is generated in situ after implantation. In general, prefabricated porous materials display weaker mechanical strength than the corresponding solid material, whereas materials rendered porous in situ may suffer uncontrolled mechanical failure after degradation of the component.

It is to be understood that if any prior art publication is referred to herein, such reference does not constitute an admission that the publication forms a part of the common general knowledge in the art in Australia or any other country.

SUMMARY

The invention utilises a multi-calcium salt resorption gradient that induces gradual pore formation in the calcified tissue substitute, thereby inducing new bone formation in vivo without compromising mechanical properties of the calcified tissue substitute.

Accordingly, a first aspect provides a method for producing a calcified tissue substitute, the method comprising:
   reacting ground nacre, monocalcium phosphate, and water to produce brushite;
   grinding the brushite;
   reacting ground nacre with the ground brushite in disodium hydrogenphosphate solution.

A second aspect provides a calcified tissue substitute when produced by the method of the first aspect.

A third aspect provides use of ground nacre, monocalcium phosphate, and water in the manufacture of a calcified tissue substitute for repairing a calcified tissue.

A fourth aspect provides a method for repairing a calcified tissue, the method comprising contacting the calcified tissue with the substitute of the second aspect.

An alternative form of the fourth aspect provides the substitute of the second aspect for use in a method for repairing a calcified tissue, the method comprising contacting the calcified tissue with the substitute.

In an embodiment of any one of the aspects, the calcified tissue is tooth or bone.

A fifth aspect provides a delivery device comprising a first chamber and a second chamber, the first chamber comprising ground nacre and the second chamber comprising ground brushite, wherein the ground brushite is produced by reacting ground nacre, monocalcium phosphate, and water and grinding the resulting brushite, wherein the device is adapted to deliver the ground nacre and the ground brushite simultaneously in reacting proximity thereby causing the ground nacre and the ground brushite to react in the presence of disodium hydrogenphosphate solution.

BRIEF DESCRIPTION OF THE FIGURES

FIG. 2A depicts the compressive peak load (N) and FIG. 2B depicts the compressive strength (MPa) of the samples of calcified tissue substitute (nacre-orthophosphate particles) prepared according to example 2 and a porous commercial product (SKELITE™).

FIG. 6 comprises laser confocal scanning microscope micrographs and analyses of MLO-Y4 cells cultured for 72 hours on the calcified tissue substitute E (turquoise) prepared according to example 2 using nacre particles, brushite particles and tetracalcium phosphate in the ratio 10:5:5. F-actin in cell membranes was labelled with fluorescent phalloidin (red). A. 3D structure of the cells' adhesion to the calcified tissue substitute. B. 3D structure of a single cell's adhesion to the calcified tissue substitute showing dendritic process of an osteocyte, with white arrows identifying the cell, the dendritic process, and the calcified tissue substitute.

Figure 7:
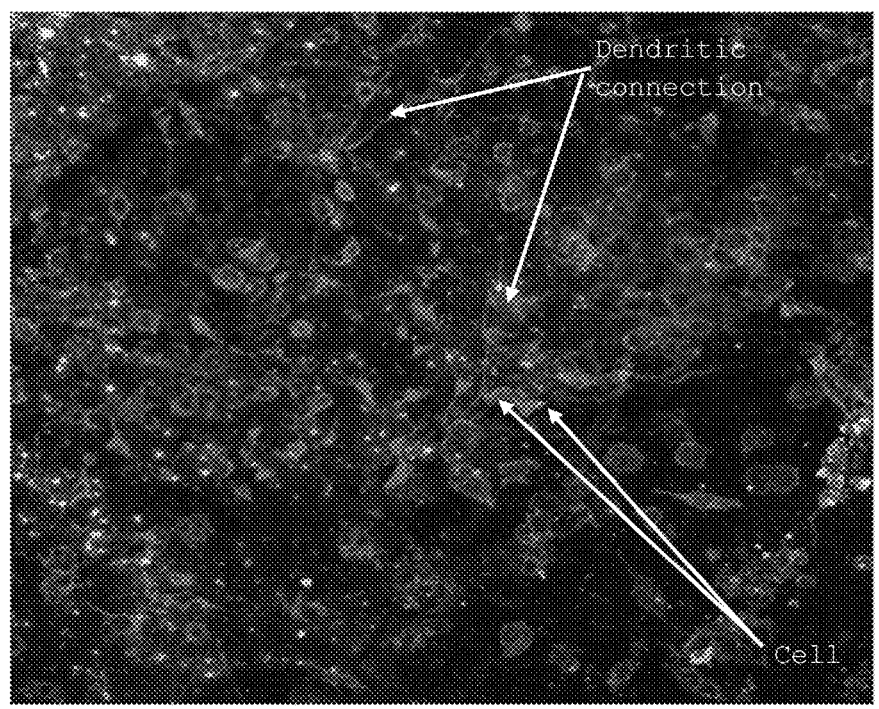

FIG. 7 is a laser confocal scanning microscope micrograph and analysis of MLO-Y4 cells cultured for 72 hours on the calcified tissue substitute A prepared according to example 2 using nacre particles, brushite particles and tetracalcium phosphate in the ratio 6:9:5. F-actin in cell membranes was labelled with fluorescent phalloidin (red). The micrograph shows dendrite connections (network) of osteocytes. White arrows identify dendritic connections and cells.

Figure 8:
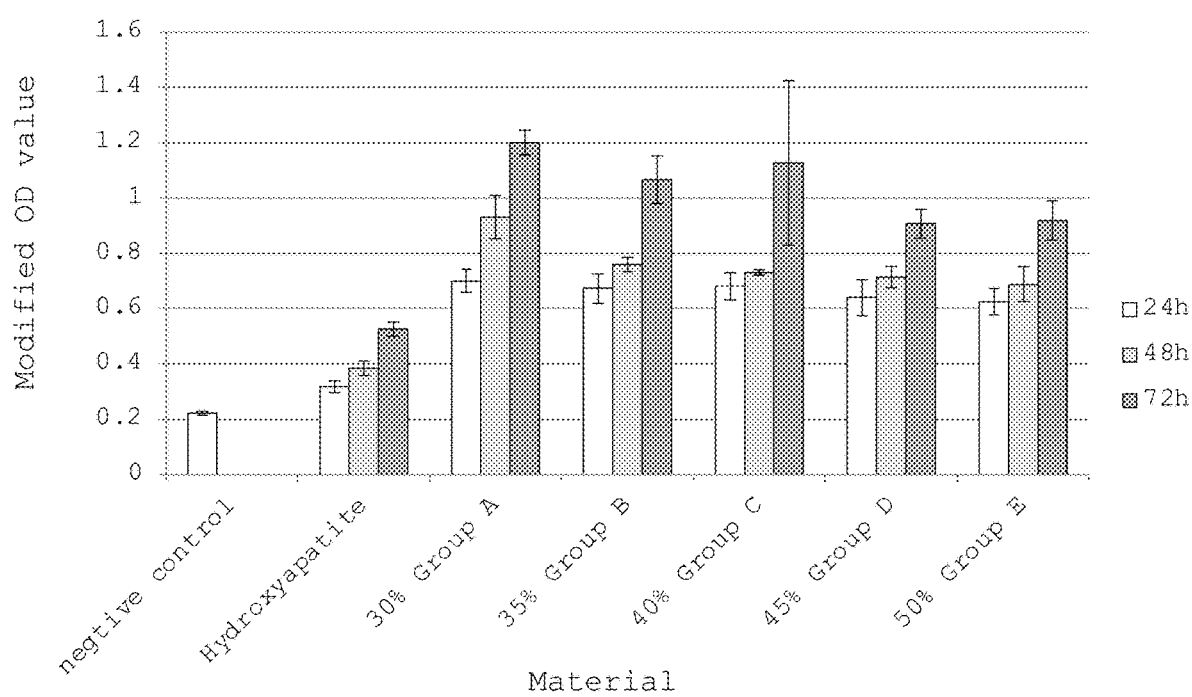

FIG. 8 is a column graph depicting cell viability of MC3T3 cells cultured up to 72 hours on the calcified tissue substitutes (nacre-calcium orthophosphate material) prepared according to example 2. Cell viability was determined using the colorimetric MTS assay.

Figure 9:
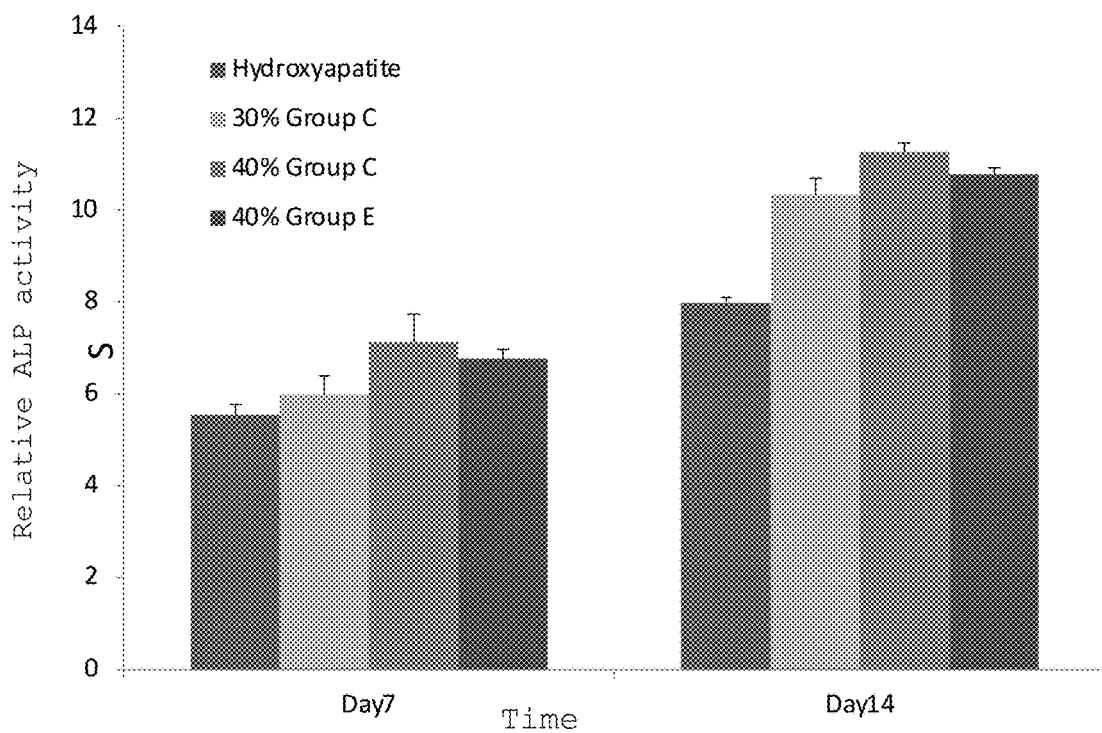

FIG. 9 is a column graph indicating cell ALP activity of MC3T3 cells cultured for 7 days and 14 days on the calcified tissue substitutes A, C and E (nacre-calcium orthophosphate material) prepared according to example 2 (in the ratio 6:9:5, 8:7:5, and 10:5:5, respectively). The activity of osteogenic differentiation marker alkaline phosphatase (ALP) was determined by quantifying the amount of p-nitrophenol, the yellow-coloured end product of hydrolysis of p-nitrophenyl phosphate, using an ALP microplate test kit according to the manufacturer's instructions (Nanjing Jiancheng Bioengineering Institute, Nanjing, People's Republic of China).

Figure 10:
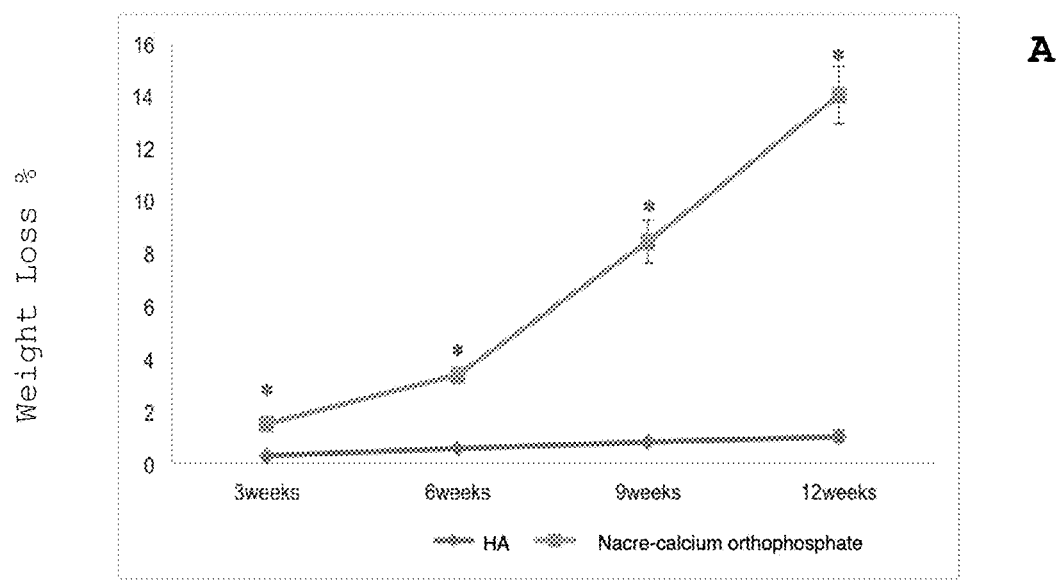
Figure 10:
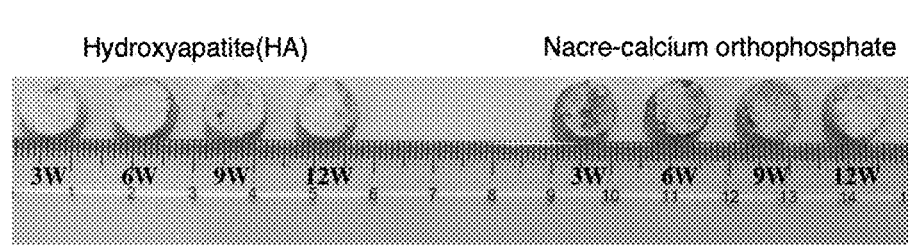

FIG. 10 comprises a line chart (A) depicting the in vivo biodegradation rate of hydroxyapatite and nacre-calcium orthophosphate (percent weight loss over time), and the naked eye morphology of degraded material of hydroxyapatite and nacre-calcium orthophosphate (B). *indicates a statistically significant difference between nacre-calcium orthophosphate and hydroxyapatite ($P<0.05$).

Figure 11:
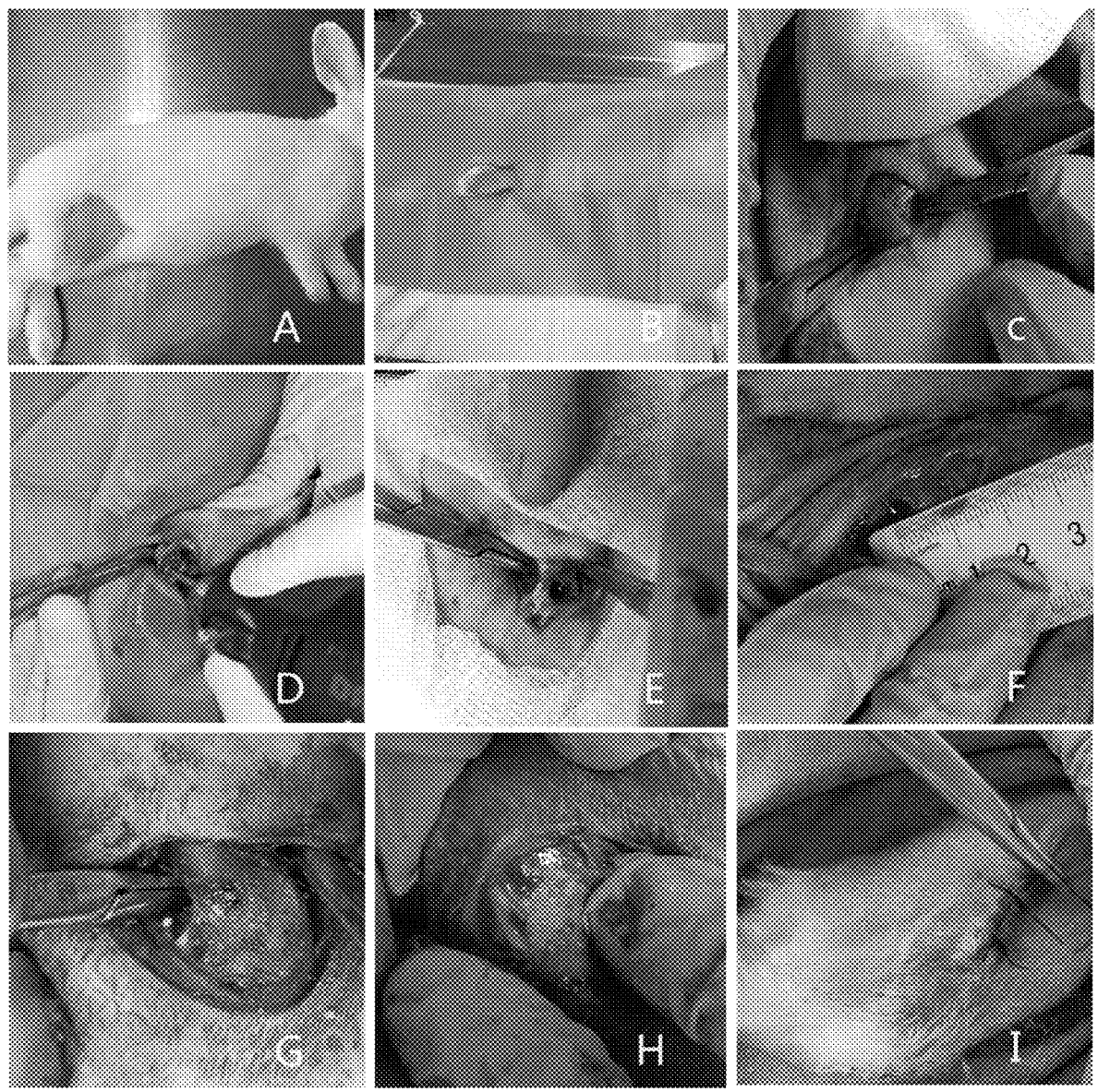

FIG. 11 comprises photographs depicting the surgical procedure of the animal model of bone defect on rabbit femoral cortical bone of example 2, part 4. FIG. 11A shows the surgery position and shaving of the anaesthetized rabbit. FIG. 11B shows the preoperative preparation of the rabbit. FIG. 11C shows exposure of the femoral cortical bone on distal metaphysis region. FIG. 11D shows drilling to make the artificial bone defect. FIG. 11E shows the basic shape of the bone defect, which is a circular and transfixed cortical bone defect. FIG. 11F shows the diameter of the bone defect is 5 mm. FIG. 11G shows the nacre-calcium orthophosphate implanted bone defect. FIG. 11H shows the hydroxyapatite implanted bone defect. FIG. 11I shows suturing the incision.

Figure 12:
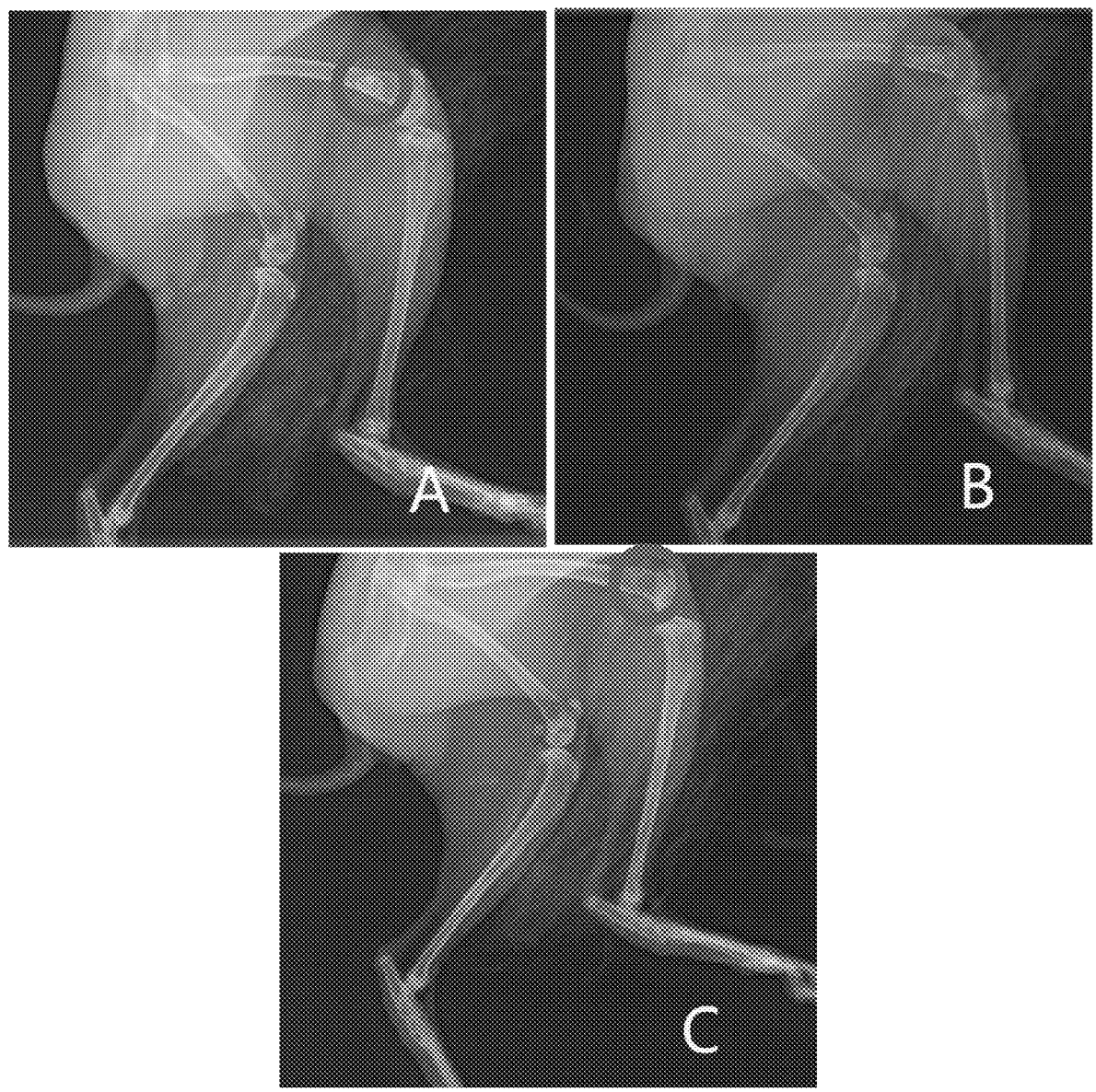
Figure 12:
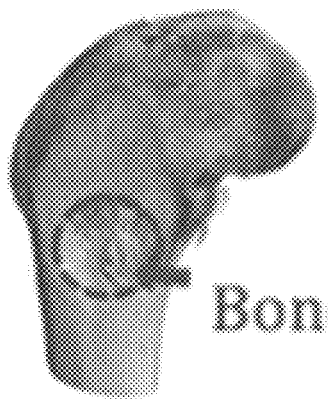
Figure 12:
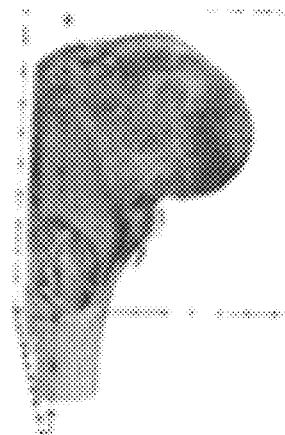

FIG. 12 comprises imaging confirmation of the animal model. Circles highlight the bone defect sites. FIG. 12A is the X-ray image of nacre-calcium orthophosphate implanted group. FIG. 12B is the X-ray image of hydroxyapatite-implanted group. FIG. 12C is the X-ray image of the blank control group. FIG. 12D is Micro-CT scan of a sample of the surgery control group, which clearly shows the diameter of the bone defect is 5 mm.

Figure 13:
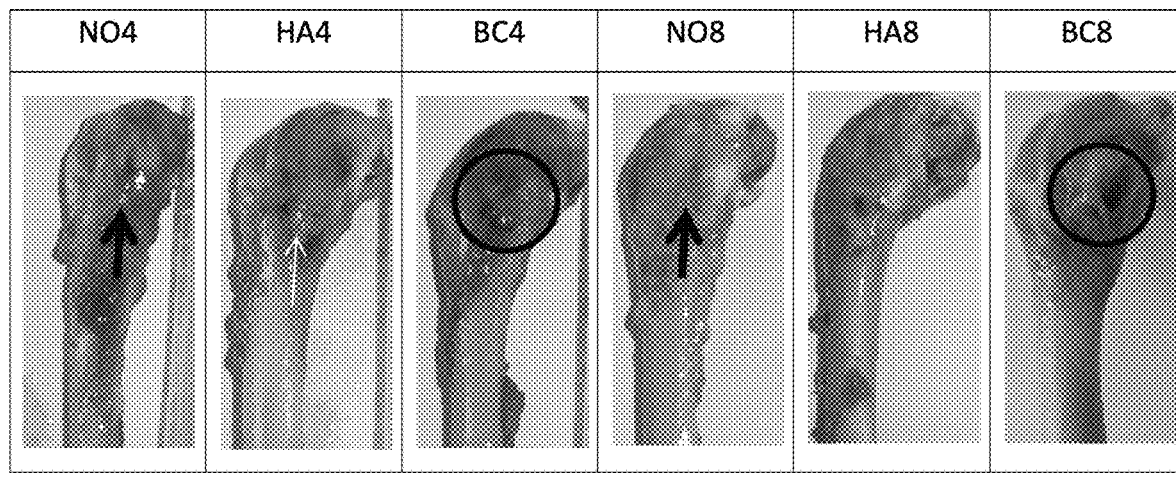

FIG. 13 comprises photographs depicting the morphology of samples retrieved from the animal model. The black arrows point to the nacre-calcium orthophosphate particles that remained at bone defect sites. The white arrow points to the hydroxyapatite particles that remain at the bone defect site. The circles indicate the bone defect site of the control group.

Figure 14:
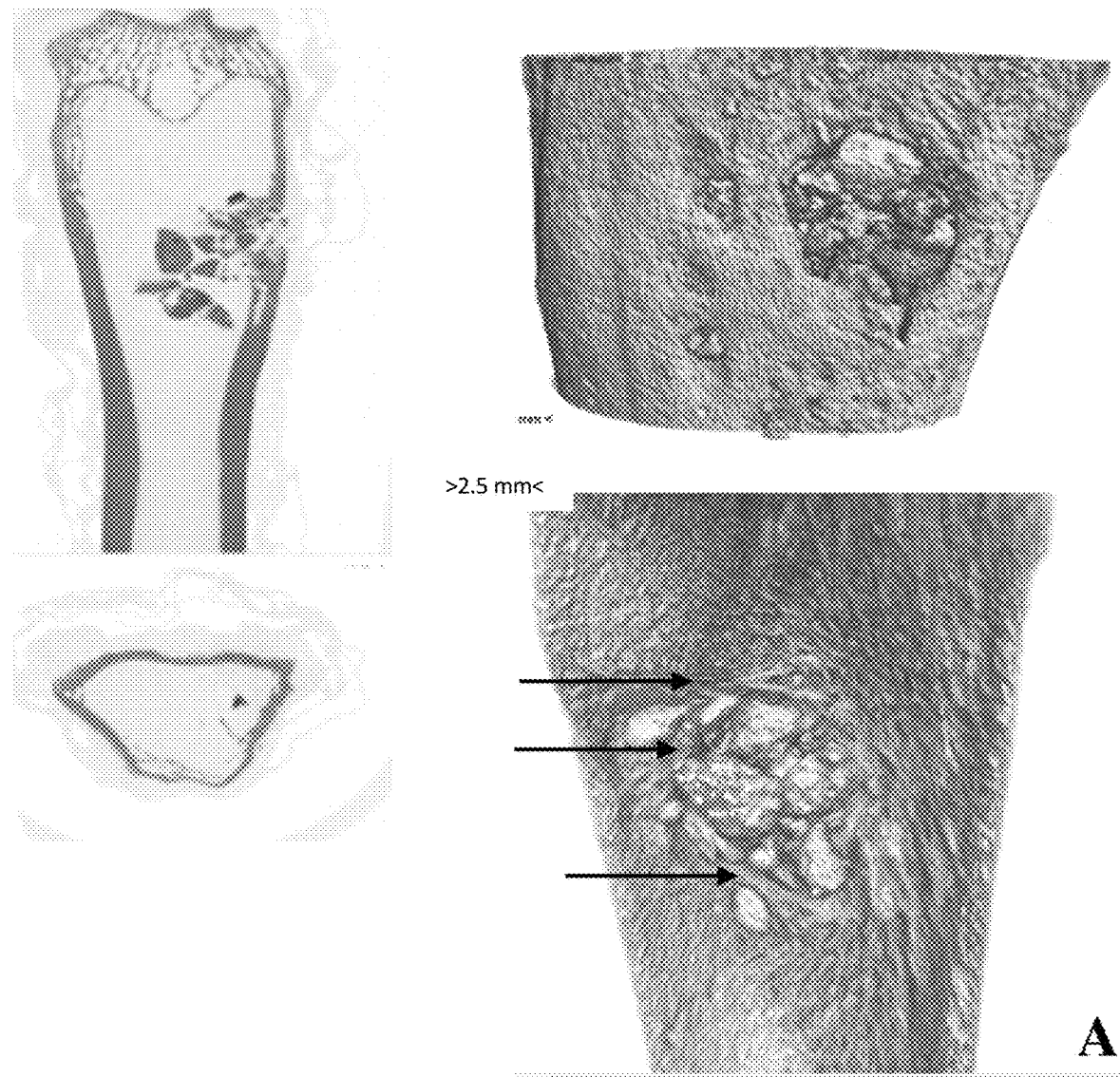
Figure 14:
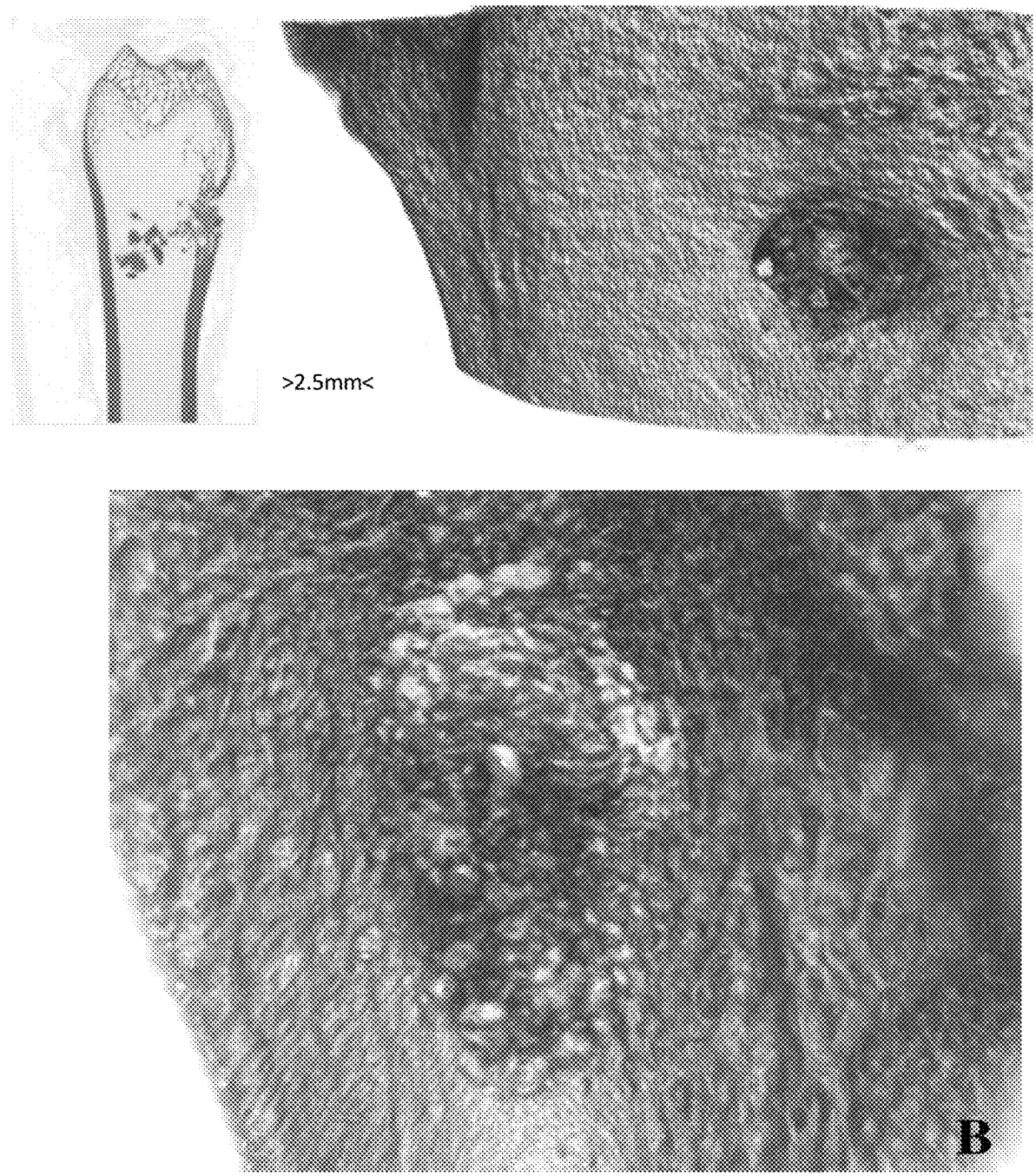
Figure 14:
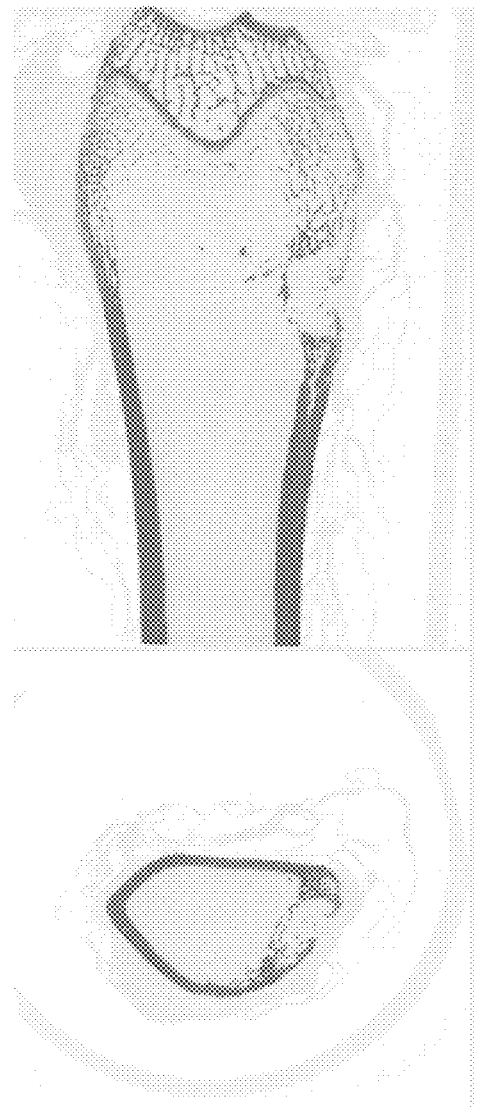
Figure 14:
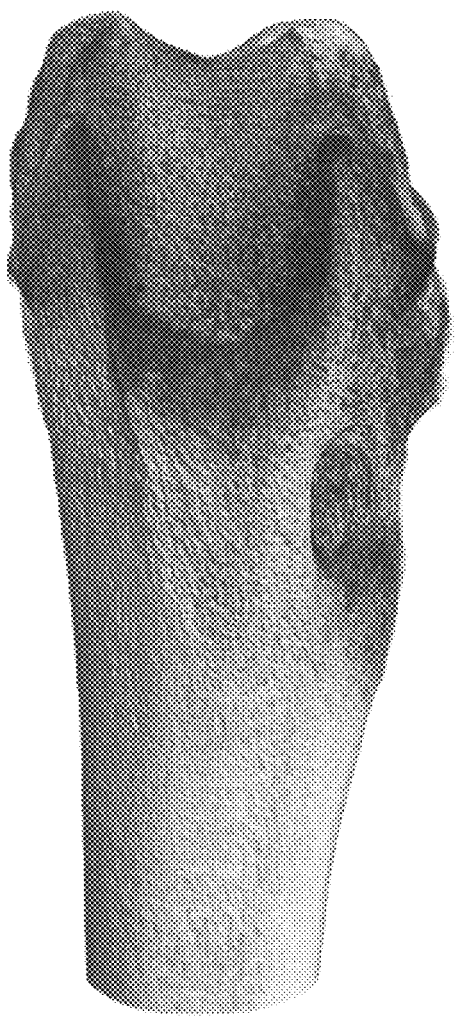
Figure 14:
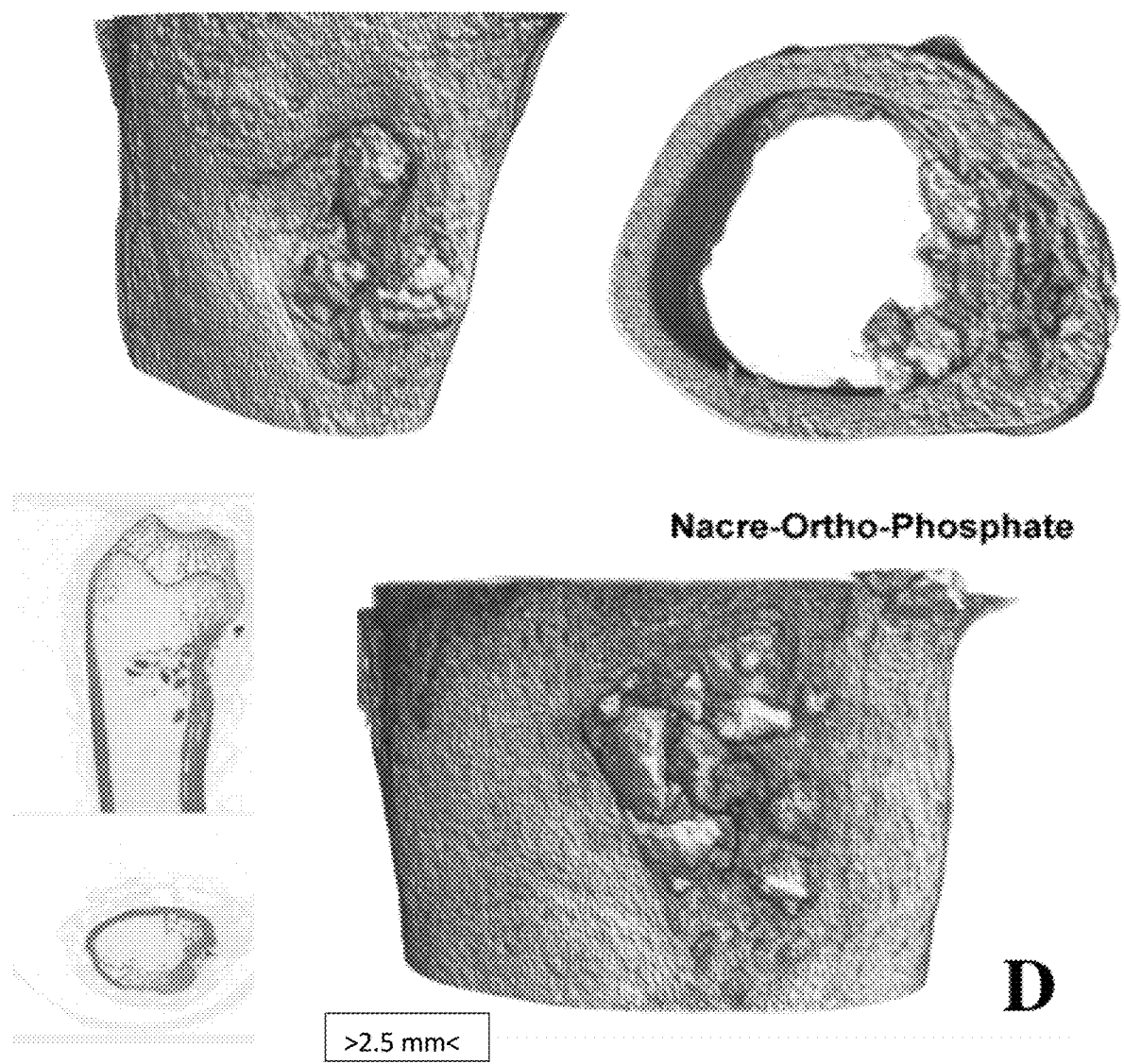
Figure 14:
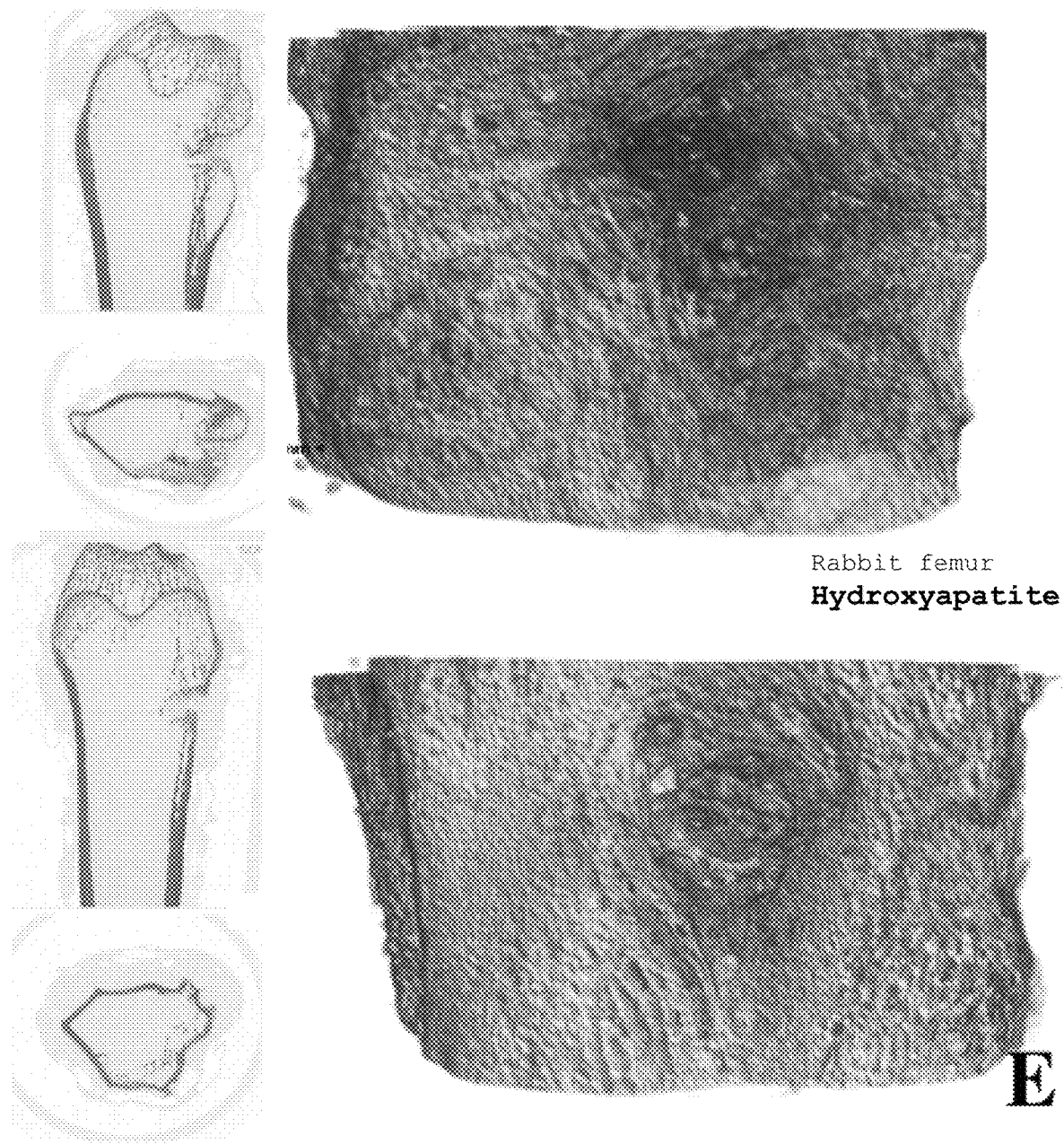
Figure 14:
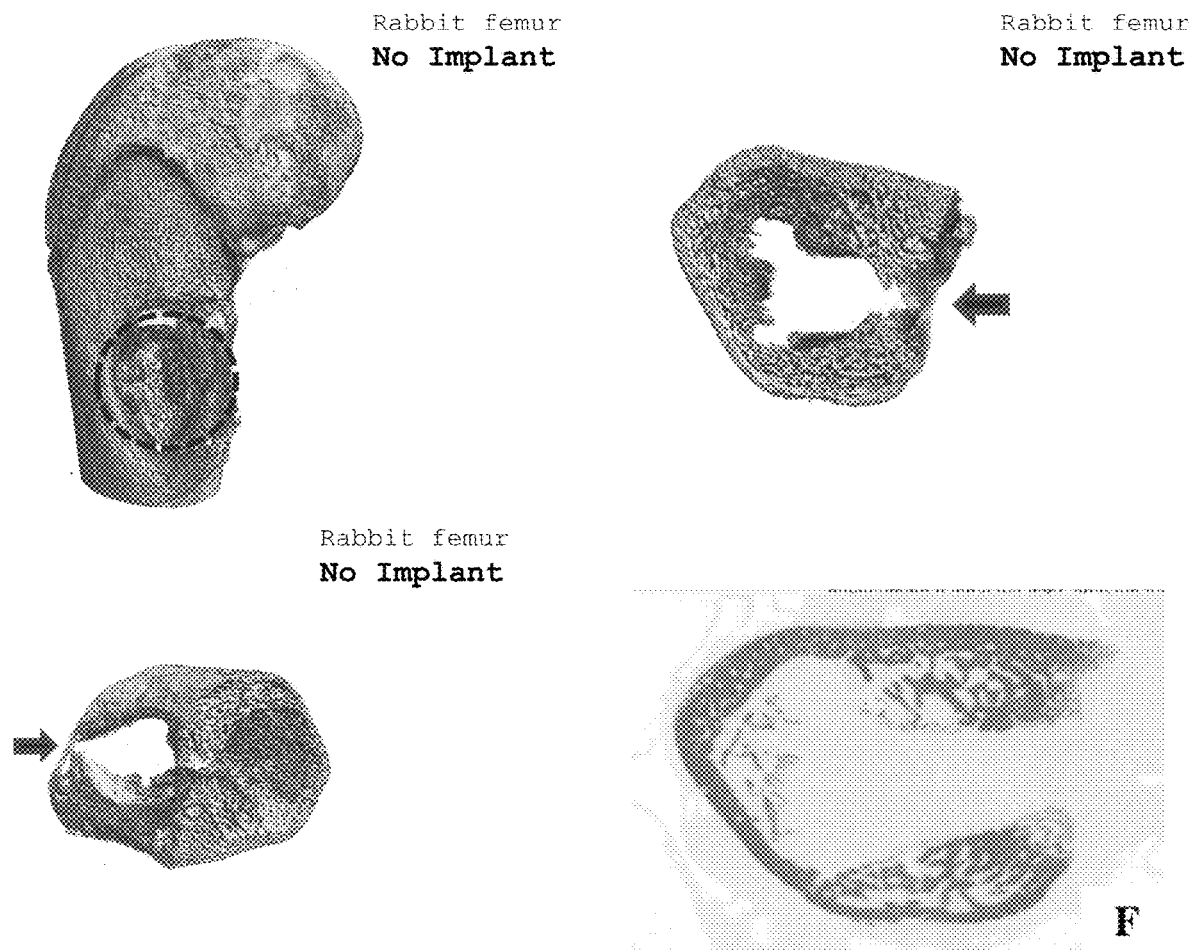

FIG. 14 comprises a series of images indicating that potent osteoblast activity was stimulated by the calcified tissue substitutes of the disclosure. FIG. 14A to 14F comprises the sagittal plane 2D Micro-CT image and 3D reconstruction image of group:
- A—NO4 (4 weeks nacre-calcium orthophosphate implanted group)—the black arrows point to the new bone trabecula structure;
- B—HA4 (4 weeks hydroxyapatite-implanted group);
- C—BC4 (4 weeks blank control group);
- D—NO8 (8 weeks nacre-calcium orthophosphate implanted group);
- E—HA8 (8 weeks hydroxyapatite-implanted group); and
- F—BC8 (8 weeks blank control group).

Figure 15:
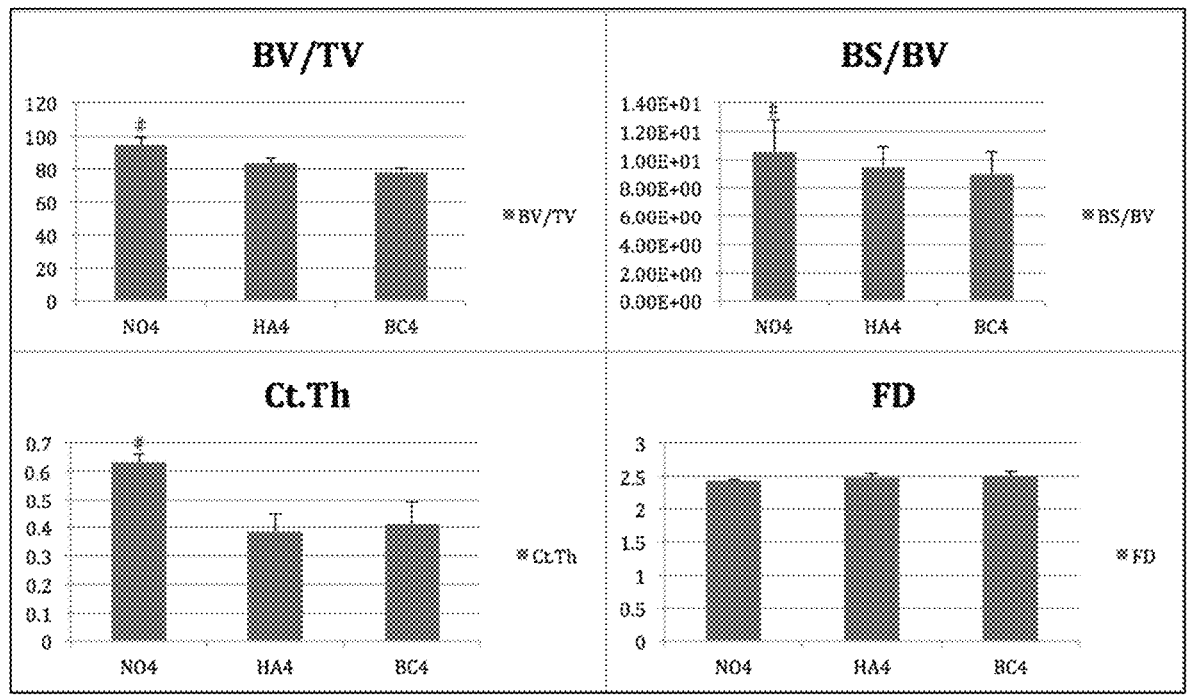

FIG. 15 comprises column graphs showing analysis of Micro-CT after 4 weeks for NO4, HA4 and BC4 groups. The Bone Volume/Total Volume (BV/TV), Bone Surface/Bone Volume (BS/BV), Cortical Thickness (Ct.Th), Fractal dimension (FD) are presented. # indicates a statistically significant difference between nacre-calcium orthophosphate and hydroxyapatite ($P<0.05$).

Figure 16:
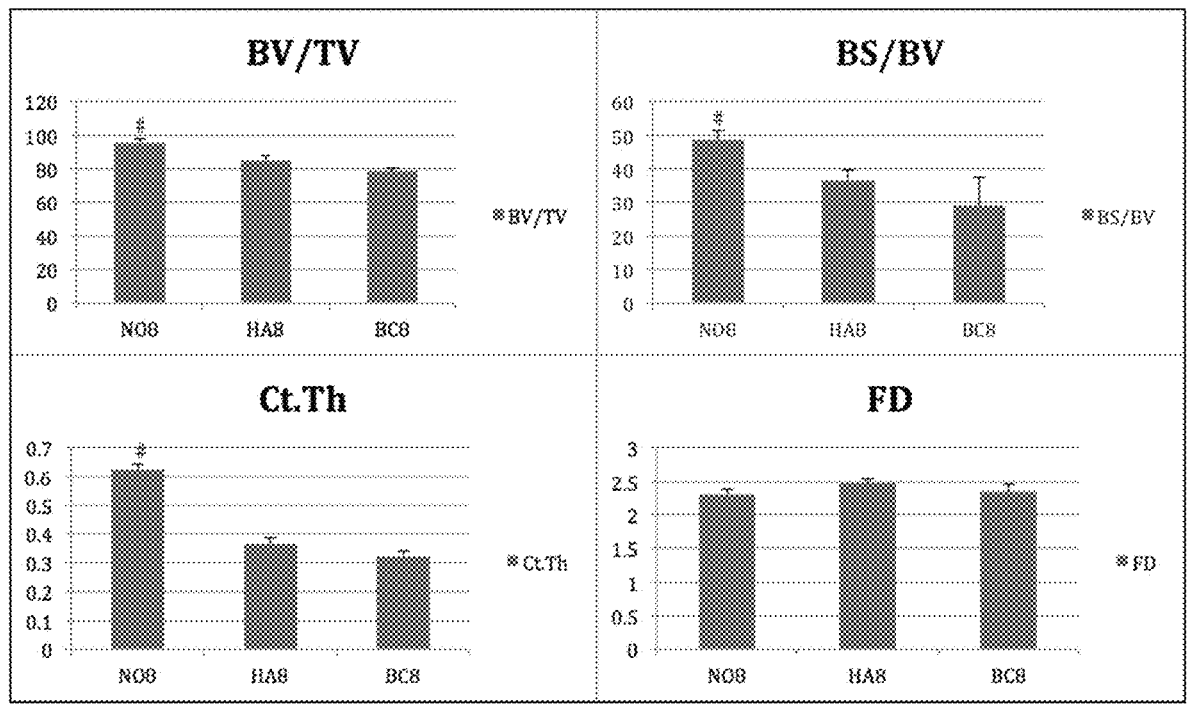

FIG. 16 comprises column graphs showing analysis of Micro-CT after 8 weeks for NO8, HA8 and BC8 groups. The Bone Volume/Total Volume (BV/TV), Bone Surface/Bone Volume (BS/BV), Cortical Thickness (Ct.Th), Fractal dimension (FD) are presented. # indicates a statistically significant difference between nacre-calcium orthophosphate and hydroxyapatite ($P<0.05$).

Figure 17:
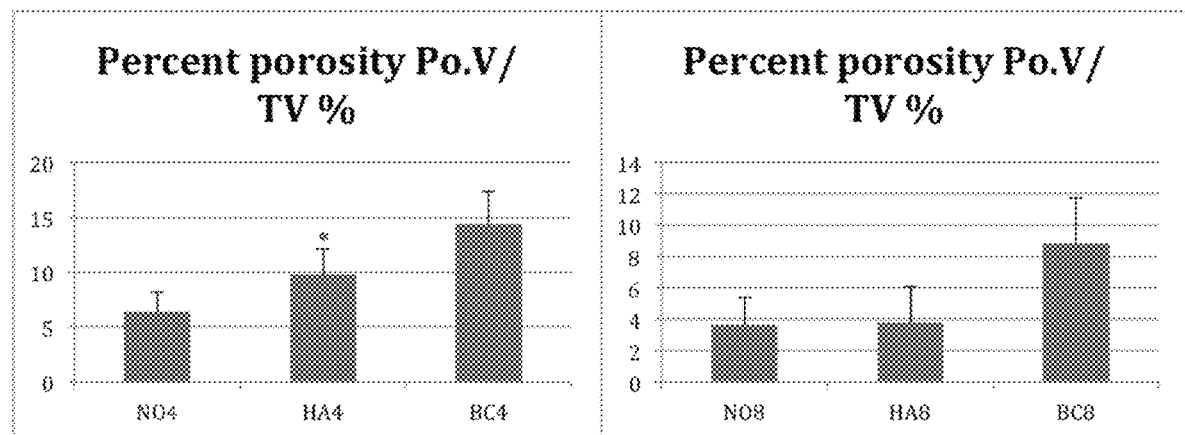

FIG. 17 comprises column graphs showing analysis of the Micro-CT data of percent porosity for bone defect sites after 4 weeks for NO4, HA4 and BC4 groups and after 8 weeks for NO8, HA8 and BC8 groups. # indicates a statistically significant difference between nacre-calcium orthophosphate and hydroxyapatite. ($P<0.05$)

DETAILED DESCRIPTION

The inventors have developed an improved calcified tissue substitute for repair of calcified tissue and a method for manufacturing the calcified tissue substitute. The invention utilises the different degradation time of the main components to convert the solid material into a porous structure in vivo. Namely, in the components, the remaining nacre particles have the fastest degradation rate, which begins to biodegrade through contact with body fluid. Once the dissolution of nacre occurs, the bioactive matrix will release, enhancing cell integration and inducing bone formation. Simultaneously, pores are generated allowing cell ingrowth. Brushite (or monetite), carbonated-apatite, and strontium substituted hydroxyapatite, which are other components of the calcified tissue substitute of the disclosure, have different solubilities compared to nacre, and these components will be biodegraded in 2 to 8 months. These different calcium orthophosphates will be gradually absorbed by the cellular activity of macrophages, osteoclasts and other cell types via phagocytosis and the body fluid-solid reaction, thereby increasing porosity and cell ingrowth. Finally, hydroxyapatite in the calcified tissue substitute can be kept in body for up to 2 years as an osteoconductive scaffold and entirely replaced by new bone by means of the cell-mediated resorption afterwards. If used, the bioinert drug carrier laponite will remain in the body.

Table 1 provides biodegradation rates of nacre-orthophosphate components that enable generation of a porous structure in the material surface in situ and thus allow cell and tissue ingrowth for calcified tissue repair.

TABLE 1

Biodegradation of nacre-orthophosphates in the composition of bone substitute.

| Component | Estimated degradation peak-time | Mean mechanism of action |
|---|---|---|
| Nacre (aragonite) | 2-6 weeks | Fluid-solid reaction |
| Brushite or monetite* | 2-4 months | Cell mediated resorption & Fluid-solid reaction |
| Carbonated-apatite | 3-6 months | Cell mediated resorption & Fluid-solid reaction |
| Strontium substituted hydroxyapatite | 4-8 months | Cell mediated resorption |
| Hydroxyapatite | 5-24 months | Cell mediated resorption |
| Laponite | No degradation | Non-biodegradable |

*Dicalcium phosphate dehydrate (DPCD) or Dicalcium phosphate anhydrous (DPCA)

The invention overcomes the lack of sufficient osteoconductivity and osteoinductivity and rapid resorption of nacre by providing a method for coating calcium orthophosphate on the surface of nacre particles and by providing nacre particles coated with calcium orthophosphate made by the method. The invention also provides controlled co-release from the calcium orthophosphate-coated nacre particles of positively charged antibodies or molecules loaded onto appropriate additive particles, e.g. laponite particles.

Without wishing to be bound by theory, the unreacted nacre in the calcified tissue substitute comprises bioactive compounds, thereby enhancing osteoinductivity. Further, exposed nacre is resorbed more rapidly than other calcium orthophosphates. The resorption gradient of four main different components offers a gradually pore-forming process that is accompanied by new bone formation after implantation. Compared with prior porous bone substitutes, traditionally made of calcium salt material, pores of the calcified tissue substitute of the invention are generated in vivo, thereby providing a stronger mechanical support in early stages of calcified tissue repair and enhancing osteoconductivity.

In use, the calcified tissue substitute develops pores in vivo owing to faster resorption of nacre relative to calcium orthophophate, which solves the problem of slow resorption of calcium phosphate-based commercial products that hinders osteogenesis.

In any of the aspects of the invention, the calcified tissue may be a bone or a tooth.

As used herein, "repair" includes mending, restoring, reconstructing or rehabilitating the calcified tissue.

Repair may be needed due to infection, trauma, inflammation, or tumorous or congenital aetiologies.

As used herein, "repairing a calcified tissue" encompasses practices that ultimately treat another tissue or organ, for example spinal fusion where the object is to alleviate spinal canal narrowing and spinal cord and/or spinal nerve squeezing.

As used herein, a calcified tissue "substitute" refers to a material contacted with a calcified tissue to promote repair of the calcified tissue through osteogenesis, osteoconduction and/or osteoinduction. A calcified tissue "substitute" may also be referred to as nacre-calcium orthophosphate or a calcified tissue graft. In one embodiment, the calcified tissue substitute is used to fill a void.

As used herein, the term "osteogenesis" refers to the development and formation of calcified tissue. The process of osteogenesis may involve osteoconduction and/or osteoinduction.

The term "osteoconduction" refers to the passive process by which bone forming cells near the site of implantation move across a scaffold, i.e. the calcified tissue substitute, and replace the scaffold with new calcified tissue over time. Osteoconductive materials allow osteoblasts and osteoclasts to attach, migrate, grow and/or divide.

The term "osteoinduction" refers to the active process by which a calcified tissue substitute or graft recruits bone-forming cells to the site of implantation and induces them to form new bone. Osteoinduction refers to attraction, proliferation, and differentiation of early-lineage cells (e.g., mesenchymal stem cells or osteoprogenitor cells) into bone-forming cells, resulting in the formation of new calcified tissue.

The method for manufacturing the calcified tissue substitute uses nacre as a starting material and a further reactant, and the manufactured calcified tissue substitute comprises nacre. Nacre is an organic/inorganic biocomposite of aragonite mineral comprising calcium carbonate ($CaCO_3$) and bioactive agents.

The nacre is ground or milled to a specific particle size distribution and then reacted with monocalcium phosphate, optionally as the hydrate ($Ca(H_2PO_4)_2 \cdot H_2O$), to form brushite crystals. The brushite crystals are ground or milled to a specific particle size distribution. The brushite crystals are optionally dried prior to grinding or milling. In one embodiment, the particle size of the ground brushite is less than the particle size of the ground nacre.

Without wishing to be bound by theory, the nacre particle size appears to be important in manufacturing the calcified tissue substitute. The particle size affects setting time—the finer the ground nacre particles, the faster the setting time of the calcified tissue substitute. Accordingly, the particle size of the ground nacre, and therefore the setting time of the calcified tissue substitute, may be adapted according to the repair required for the calcified tissue, inasmuch as different repair applications require different setting times.

Nacre and brushite may be ground or milled by ball milling, optionally high energy ball milling or planetary ball milling.

In one embodiment, the ground nacre particle size is about 1000 µm or less, about 900 µm or less, about 800 µm or less, about 700 µm or less, about 600 µm or less, about 500 µm or less, about 400 µm or less, about 300 µm or less, about 200 µm or less, about 100 µm or less, about 50 µm or less, or about 10 µm or less.

In one embodiment, the ground nacre particle size is about 1 µm or more, about 5 µm or more, about 10 µm or more, about 15 µm or more, about 20 µm or more, about 30 µm or more, about 40 µm or more, about 50 µm or more, about 60 µm or more, about 70 µm or more, about 80 µm or more, about 90 µm or more, or about 100 µm or more.

In one embodiment, the ground nacre particle size is about 50 µm to about 100 µm, about 50 µm to about 200 µm, about 50 µm to about 300 µm, about 50 µm to about 400 µm, or about 50 µm to about 500 µm.

In one embodiment, the ground brushite particle size is about 500 µm or less, about 400 µm or less, about 300 µm or less, about 200 µm or less, about 100 µm or less, about 90 µm or less, about 80 µm or less, about 70 µm or less, about 60 µm or less, about 50 µm or less, about 40 µm or less, about 30 µm or less, about 20 µm or less, about 10 µm or less, about 9 µm or less, about 8 µm or less, about 7 µm or less, about 6 µm or less, about 5 µm or less, about 4 µm or less, about 3 µm or less, about 2 µm or less, or about 1 µm or less.

In one embodiment, the ground brushite particle size is about 1 µm or more, about 2 µm or more, about 3 µm or more, about 4 µm or more, about 5 µm or more, about 6 µm or more, about 7 µm or more, about 8 µm or more, about 9 µm or more, about 10 µm or more, about 15 µm or more, about 20 µm or more, about 30 µm or more, about 40 µm or more, about 50 µm or more, about 60 µm or more, about 70 µm or more, about 80 µm or more, about 90 µm or more, or about 100 µm or more.

In one embodiment, the ground brushite particle size is about 10 µm to about 20 µm, about 10 µm to about 30 µm, about 10 µm to about 40 µm, about 10 µm to about 50 µm, about 10 µm to about 60 µm, about 10 µm to about 70 µm, about 10 µm to about 80 µm, about 10 µm to about 90 µm, about 10 µm to about 100 µm, about 10 µm to about 150 µm, or about 10 µm to about 200 µm.

In one embodiment, the calcified tissue substitute has a particle size of about 5 mm. In another embodiment, the calcified tissue substitute has a particle size of about 1 µm, about 5 µm, about 10 µm, about 50 µm, about 100 µm, about 500 µm, about 1 mm, about 2 mm, about 3 mm, about 4 mm, about 5 mm, about 6 mm, about 7 mm, about 8 mm, about 9 mm, or about 10 mm.

As used herein, "particle" and "particulate" refers to separate constituent units, but does not preclude the particles being fused into a solid. Therefore, "particle" and "particulate" refers to ground nacre and ground brushite as well as the calcified tissue substitute comprising fused nacre particles coated or surrounded by calcium orthophosphate. The particles may be a powder.

As used herein, "particle size" refers to the pore size of a selective mesh through which the particle passes. It follows that ground nacre and ground brushite having defined particle sizes may be selected by sieving using one or more meshes having defined pore sizes. Sieving and meshes are known in the art.

In one embodiment, the ground nacre and monocalcium phosphate are reacted in a ratio of about 4:10. In another embodiment, the ground nacre and monocalcium phosphate are reacted in a ratio of about 4:5, about 4:6, about 4:7, about 4:8, about 4:9, about 4:11, about 4:12, about 4:13, about 4:14, about 4:15, about 0.5:10, about 1:10, about 2:10, about 3:10, about 5:10, about 6:10, about 7:10, about 8:10, or about 9:10.

In one embodiment, the ground nacre and monocalcium phosphate are reacted at room temperature. In another embodiment, the ground nacre and monocalcium phosphate are reacted at about 4° C., about 10° C., about 15° C., about 20° C., about 25° C., about 30° C., about 35° C., about 37° C., about 40° C., about 42° C., about 50° C., or about 60° C.

If dried before grinding, the brushite crystals may be air-dried or freeze-dried, for example.

In the second stage of the method, additional ground nacre is mixed with the ground brushite and reacted in disodium hydrogenphosphate ($Na_2HPO_4$) solution.

In one embodiment, the disodium hydrogenphosphate solution has a pH of about 8.2 to about 9.5. In one embodiment, the disodium hydrogenphosphate solution has a pH of about 7.5, about 7.6, about 7.7, about 7.8, about 7.9, about 8, about 8.1, about 8.2, about 8.3, about 8.4, about 8.5, about 8.6, about 8.7, about 8.8, about 8.9, about 9, about 9.1, about 9.2, about 9.3, about 9.4, about 9.5, about 9.6, about 9.7, about 9.8, about 9.9, about 10, about 10.2, about 10.4, about 10.6, about 10.8, or about 11. In one embodiment, the disodium hydrogenphosphate solution has a pH of about 9.25.

In one embodiment, the disodium hydrogenphosphate solution is a 2.5% to 4% solution. In another embodiment, the disodium hydrogenphosphate solution is about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10%.

In one embodiment, the ground nacre and ground brushite are reacted in a ratio of about 4:10. In another embodiment, the ground nacre and ground brushite are reacted in a ratio of about 4:5, about 4:6, about 4:7, about 4:8, about 4:9, about 4:11, about 4:12, about 4:13, about 4:14, about 4:15, about 0.5:10, about 1:10, about 2:10, about 3:10, about 5:10, about 6:10, about 7:10, about 8:10, or about 9:10.

In a further embodiment of the second stage of the method, the reaction of ground nacre with the ground brushite in disodium hydrogenphosphate solution further comprises tetracalcium phosphate ($Ca_4(PO_4)_2O$). There are three advantages in using tetracalcium phosphate in this stage: it reacts quickly with brushite to form hydroxyapatite, which leads to the initial setting; it may catalyse the reaction between nacre and brushite; and it offers a different resorption rate than nacre, brushite and carbonate apatite. The resorption gradient aids gradual generation of pores in the calcified tissue substitute after implantation.

In one embodiment, tricalciumphosphate ($\alpha$-TCP) is used in place of tetracalcium phosphate, as $\alpha$-TCP converts to hydroxyapatite through a hydration reaction.

In one embodiment, the ground nacre, ground brushite, and tetracalcium phosphate are reacted in a ratio of 6:9:5, 7:8:5, 8:7:5, 9:6:5, or 10:5:5 in disodium hydrogenphosphate solution.

As shown in example 2, varying the ratio of the ground nacre, ground brushite, and tetracalcium phosphate varies the characteristics of the calcified tissue substitute. As shown by X-ray diffraction (XRD), varying the proportion of ground nacre will vary the proportion of nacre in the calcified tissue substitute, which provides significant advantages. For instance, calcified tissue substitutes with a higher proportion of nacre, e.g. calcified tissue substitute E, will also have the highest proportion of bioactive agents and therefore the highest level of osteoinductivity, compared with calcified tissue substitutes with relatively lower proportions of nacre. As a corollary, calcified tissue substitutes with a lower proportion of nacre, e.g. calcified tissue substitute A, will have the highest proportion of apatite and therefore the highest level of osteoconductivity, compared with calcified tissue substitutes with relatively higher proportions of nacre. That is, calcified tissue substitutes with a relatively low proportion of nacre and high proportion of apatite will have a slower rate of resorption, thereby providing scaffolding or mechanical support for a longer period of time. Accordingly, the composition of the calcified tissue substitute can be varied according to the specific repair needed by the calcified tissue.

In one embodiment, the disodium hydrogenphosphate solution is reacted with other reactants in a solution:reactant ratio of about 1:4, about 1:3, about 1:2, or about 1:1, or about 10%, about 20%, about 25%, about 30%, about 33%, about 40%, about 50%, or about 60%.

In one embodiment, the ground nacre and ground brushite, and optionally tetracalcium phosphate, are reacted at about 37° C. This embodiment is particularly suited to surgery where the calcified tissue substitute is reacted and allowed to set and harden in situ. If the calcified tissue substitute is used for repair in a non-human animal whose body temperature is not 37° C., the ground nacre and ground brushite, and optionally tetracalcium phosphate, may be reacted at body temperature.

In another embodiment, the ground nacre and ground brushite, and optionally tetracalcium phosphate, are reacted at room temperature, or at about 4° C., about 10° C., about 15° C., about 20° C., about 25° C., about 30° C., about 35° C., about 37° C., about 40° C., about 42° C., about 50° C., or about 60° C. Reaction temperatures above or below about 37° C. are suited to manufacture of calcified tissue substitutes that are intended to be implanted pre-set and pre-hardened.

In one embodiment, the method further comprises adding an agent, optionally hectorite, laponite or alpha-calcium sulphate, that modifies setting time of the composition.

Such additives may also serve to provide controlled co-release from the calcified tissue substitutes (nacre-orthophosphate particles) of positively charged antibodies or molecules loaded onto appropriate additive particles, e.g. laponite particles. Such controlled co-release is known in the art (e.g. Xiao et al. *Mater Sci Eng C Mater Biol Appl* (2016) 60: 348-56; Ordikhani et al. *J Mater Sci Mater Med* (2015) 26(12): 269; Li et al. *ACS Appl Mater Interfaces* (2014) 6(15): 12328-34; Wang et al. *ACS Appl Mater Interfaces* (2014) 6(19): 16687-95).

In one embodiment, the calcified tissue substitute when produced by the method of the invention is particulate and comprises calcium orthophosphate on the particle surface.

As used herein, "orthophosphate" refers to the anion $PO_4^{3-}$, and "calcium orthophosphate" covers multiple compounds comprising calcium and orthophosphate with varying stoichiometry. In one embodiment, the calcium orthophosphate may be hydroxyapatite.

In one embodiment, the calcified tissue substitute is set at 100% humidity and 37° C., or 100% humidity and body temperature if the calcified tissue substitute is used for repair in a non-human animal whose body temperature is not 37° C. This embodiment is particularly suited to surgery where the calcified tissue substitute is reacted and allowed to set and harden in situ. In another embodiment, the calcified tissue substitute is set at about 4° C., about 10° C., about 15° C., about 20° C., about 25° C., about 30° C., about 35° C., about 37° C., about 40° C., about 42° C., about 50° C., or about 60° C. In another embodiment, the calcified tissue substitute is set at about 99%, about 98%, about 97%, about 96%, about 95%, about 94%, about 93%, about 92%, about 91%, about 90%, about 80%, about 70%, about 60%, or about 50% humidity. In another embodiment, the calcified tissue substitute is set at any combination of temperature and humidity from those recited above.

In one embodiment, the calcified tissue substitute has a peak load of greater than about 45 N. In another embodiment, the calcified tissue substitute has a peak load of greater than about 50 N, greater than about 100 N, greater than about 150 N, greater than about 200 N, greater than about 250 N, greater than about 300 N, greater than about 350 N, greater than about 400 N, greater than about 450 N, greater than about 500 N, greater than about 550 N, greater than about 600 N, greater than about 650 N, greater than about 700 N, greater than about 750 N, greater than about 800 N, greater than about 850 N, greater than about 900 N, greater than about 950 N, or greater than about 1000 N.

In one embodiment, the calcified tissue substitute has a compressive strength of greater than about 2.3 MPa. In another embodiment, the calcified tissue substitute has a compressive strength of greater than about 2.5 MPa, greater than about 3 MPa, greater than about 3.5 MPa, greater than about 4 MPa, greater than about 4.5 MPa, greater than about 5 MPa, greater than about 5.5 MPa, greater than about 6 MPa, greater than about 6.5 MPa, greater than about 7 MPa, greater than about 7.5 MPa, greater than about 8 MPa, greater than about 8.5 MPa, greater than about 9 MPa, greater than about 9.5 MPa, greater than about 10 MPa, greater than about 10.5 MPa, greater than about 11 MPa, greater than about 11.5 MPa, or greater than about 12 MPa.

As noted above, increased mechanical strength, e.g. increased peak load, reflects in part improved and prolonged osteoconduction.

In one embodiment, the calcified tissue substitute is implantable or injectable.

In one embodiment, the calcified tissue substitute has an initial setting time ($T_i$) of 30 min to 90 min. In another embodiment, $T_i$ is about 30 min, about 35 min, about 40 min, about 45 min, about 50 min, about 55 min, about 60 min, about 65 min, about 70 min, about 75 min, about 80 min, about 85 min, or about 90 min.

In one embodiment, the calcified tissue substitute has a final setting time ($T_f$) of 60 min to 120 min. In another embodiment, $T_f$ is about 60 min, about 65 min, about 70 min, about 75 min, about 80 min, about 85 min, about 90 min, about 95 min, about 100 min, about 105 min, about 110 min, about 115 min, or about 120 min.

An implantable calcified tissue substitute may be set and hardened before or after implantation. In contrast, an injectable calcified tissue substitute may be set or hardened after injection.

Injection of the calcified tissue substitute is facilitated by the delivery device of the fifth aspect. The delivery device provides means to delay setting and hardening of the calcified tissue substitute until the time of repair, often the time of surgery. The delay in setting and hardening is achieved by providing the ground brushite and ground nacre in separate chambers of the device, wherein activation of the device causes the ground brushite and ground nacre to react.

In one embodiment, the first chamber and/or the second chamber of the delivery device of the fifth aspect further comprises disodium hydrogenphosphate solution. In another embodiment, the delivery device comprises a third chamber comprising disodium hydrogenphosphate solution.

In one embodiment, delivery from the delivery device comprises mixing the ground nacre and the ground brushite.

In one embodiment, the delivery device is a syringe.

As used herein, "reacting proximity" refers to a spatial relationship sufficient to allow the ground nacre to react with the ground brushite, and may entail mixing of the ground nacre with the ground brushite to react.

The calcified tissue substitute is for use in repairing a calcified tissue of a subject.

A "subject" as used herein may be human or a non-human animal, for example a domestic, a zoo, or a companion animal. In one embodiment, the subject is a mammal. The mammal may be an ungulate and/or may be equine, bovine, cervine, ovine, canine, or feline, for example. In one embodiment, the subject is a primate. In one embodiment, the subject is human. Accordingly, the present invention has human medical application, and also veterinary and animal husbandry applications, including treatment of domestic animals such as horses, cattle and sheep, and companion animals such as dogs and cats.

It will be appreciated by the person skilled in the art that the exact manner of administering to a subject a therapeutically effective amount of the calcified tissue substitute will be at the discretion of the medical practitioner with reference to the repair needed. The mode of administration, including combination with other agents, timing of administration, and the like, may be affected by the subject's likely responsiveness to treatment, as well as the subject's condition and history.

The calcified tissue substitute will be manufactured and administered consistent with good medical practice. Factors for consideration in this context include the particular calcified tissue being repaired, the particular subject in which the calcified tissue is being repaired, the clinical status of the subject, the site of administration, the method of administration, the scheduling of administration, possible side-effects and other factors known to medical practitioners. The therapeutically effective amount of the calcified tissue substitute to be administered will be governed by such considerations.

The term "therapeutically effective amount" refers to an amount of calcified tissue substitute effective to repair a calcified tissue in a subject.

Throughout the description and claims of this specification, the word "comprise" and variations of the word, such as "comprising" and "comprises", means "including but not limited to", and is not intended to exclude other additives, components integers or steps.

The invention will now be described with reference to the following, non-limiting examples.

EXAMPLES

Example 1

The invention relates to of a number of chemical reactions with nacre particles.
1) Pearl nacre was selected and ground into powder form (ground nacre). The powder was then sieved with selective meshes with different pore size from 50 to 400 µm.
2) Selected nacre particles with particle size 50 to 100 µm were mixed with monocalcium phosphate in the ratio of 4:10 at room temperature for 30 minutes.
3) Nacre particles were reacted with monocalcium phosphate in distilled water to form brushite crystal and $CO_2$ at room temperature. The reaction occurred in a few minutes. The crystals were air-dried at room temperature for 3 days or freeze dried for 2-3 hours.
4) The brushite crystals were ground into powder with particle sizes between 10 to 100 µm (ground brushite).
5) The crystal brushite powder was mixed with nacre particles with particle size 50 to 400 µm in disodium hydrogen phosphate solution (pH 8.2~9.5) in a ratio of 4:10 at room temperature. This reaction made the mixture harden in 90 minutes at 100% humidity at 37° C.
6) Additives including synthetic hectorite (Laponite) or alpha-calcium sulfate can be added to control the setting time for different applications as injectable or implantable devices.
7) After setting, the nacre particles were seen to have hydroxyapatite on their surface.

The chemical reaction of steps (2) and (3) is:

$$CaCO_3 + Ca(H_2PO_4)_2 \cdot H_2O + 2H_2O \rightarrow 2CaHPO_4 \cdot 2H_2O + CO_2$$

The chemical reaction of step (5) is:

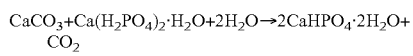
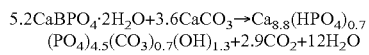

Figure 1:
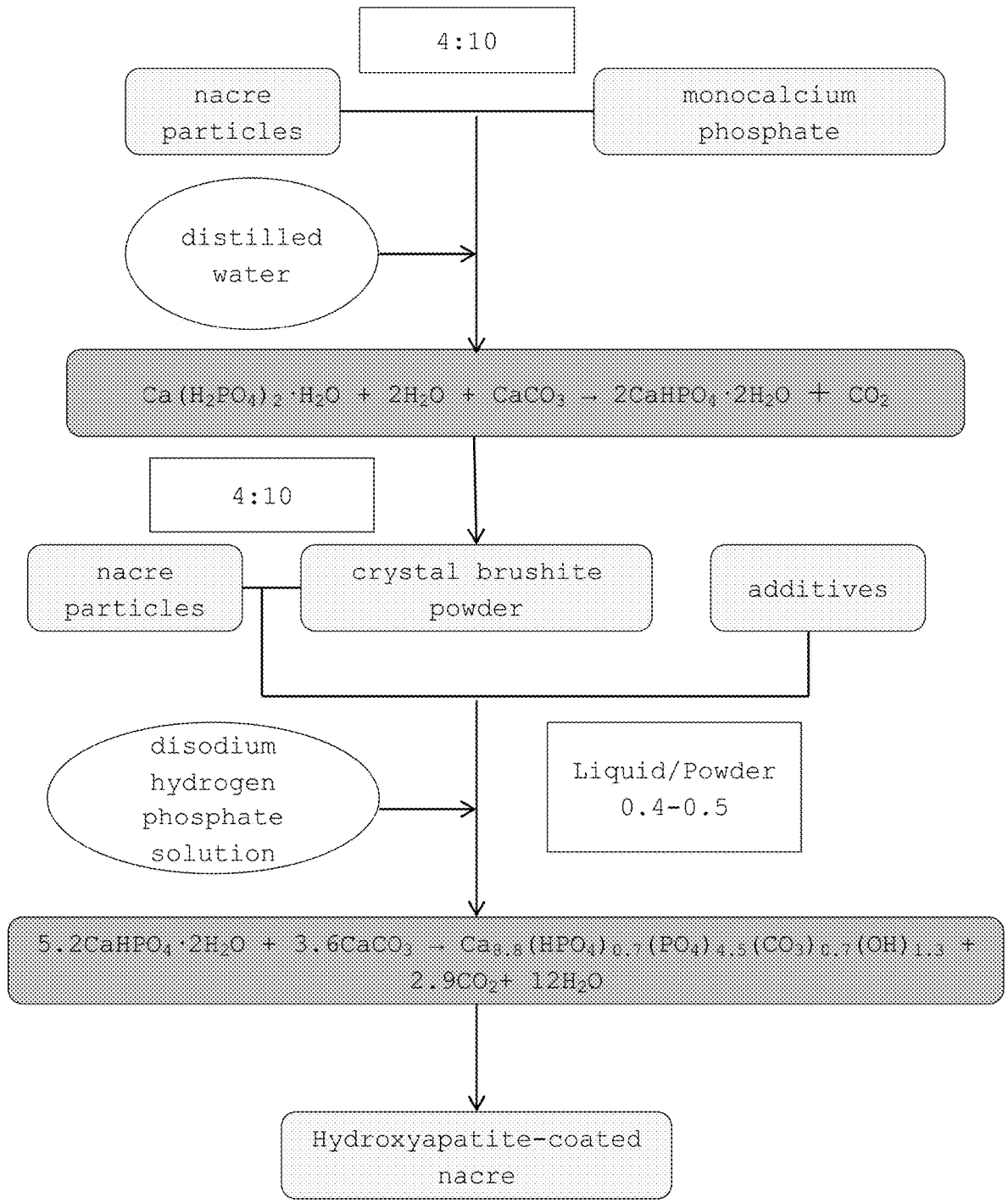
FIG. 1 is a schematic overview of the method of example 1.

An overview of the method of example 1 is provided in FIG. 1.

Example 2

1. Experimental Procedure

Nacre was selected and ground into powder form. The powder was then sieved with selective meshes with pore size under 200 µm. Nacre particles were mixed with monocalcium phosphate in a ratio of 4:10 and the mixture reacted with distilled water at room temperature to form brushite crystal and $CO_2$. The brushite crystals were dried at 37° C. then ground. As for example 1, the chemical reaction is:

$$CaCO_3 + Ca(H_2PO_4)_2 \cdot H_2O + 2H_2O \rightarrow 2CaBPO_4 \cdot 2H_2O + CO_2$$

The nacre particles were mixed with brushite particles and tetracalcium phosphate with five different ratios (A 6:9:5, B 7:8:5, C 8:7:5, D 9:6:5, E 10:5:5). The five ratios equate to 30% nacre, 35% nacre, 40% nacre, 45% nacre and 50% nacre, respectively. The mixture was reacted in 4% disodium hydrogen phosphate solution (pH 9.25) at room temperature with a liquid/powder (mL/g) ratio of 1:3. The mixed paste set and hardened at 100% humidity, 37° C. The chemical reaction is:

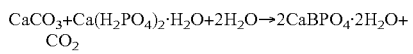

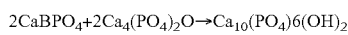
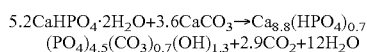

2. Physical Characterisation i. X-Ray Diffraction (XRD)

The five calcified tissue substitutes A to E were analysed by X-ray diffractometer (XRD, PANanalytical X'Pert PRO, Netherlands). Samples of each calcified tissue substitute were scanned using a step scanning method with the step size of 0.0070° in the range from 10° to 90° of the diffraction angle (2θ), the diffractometer was operated at 40 kV and 40 mA.

The XRD results (table 2) indicate the inorganic chemical composition of the nacre-calcium orthophosphate particles, i.e. the calcified tissue substitute.

TABLE 2

Composition determined by XRD of calcified tissue substitutes manufactured according to example 2.

| | Calcified tissue substitute | | | | |
|---|---|---|---|---|---|
| Compound | A | B | C | D | E |
| Nacre (starting) | 30% | 35% | 40% | 45% | 50% |
| Nacre (remaining) | 14.9% | 19.0% | 25.0% | 31.0% | 34.3% |
| Nacre Monetite | 18.8% | 18.0% | 16.0% | 14.0% | 10.1% |
| Carbonate-apatite or Apatite-(CaOH) (Na, ($CO_3$)-substituted) | 15.8% | 18.0% | 17.0% | 16.0% | 17.2% |
| Apatite (CaOH) * (including F and Sr substituted Apatite (CaOH)) | 50.5% | 45.0% | 42.0% | 39.0% | 38.4% |
| Total | 100% | 100% | 100% | 100% | 100% |
| (Sr substituted Apatite (CaOH) | 11.9% | 12.0% | 12.0% | 11.0% | 10.1%) |

The XRD data show that calcified tissue substitute E had the highest percentage of nacre, and accordingly the highest percentage bioactive composition, and therefore the highest osteoinductivity. Calcified tissue substitute A had the lowest percentage of nacre and the highest percentage of apatite.

Consequently, the resorption rate of calcified tissue substitute A is the slowest, and therefore provides mechanical support for a greater period of time and is beneficial for large calcified tissue defects.

ii. Compression Test

Figure 2:
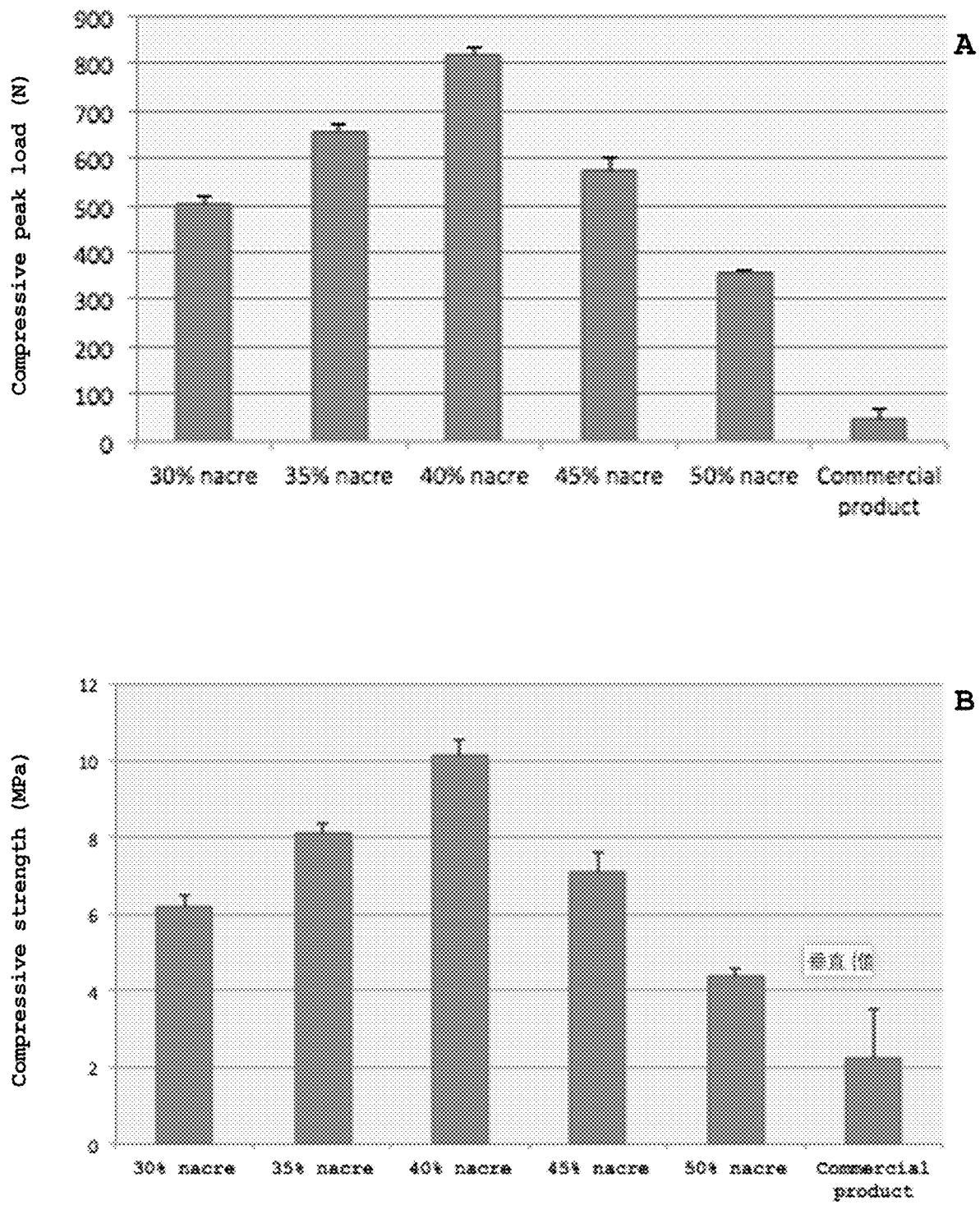
FIG. 2 comprises column graphs depicting mechanical characteristics of calcified tissue substitutes manufactured according to example 2.

Mechanical characterisation (table 3, FIG. 2) was performed on cylindrical specimens (10 mm diameter×20 mm high) held at 100% humidity and 37° C. for 3 days, and immediately submitted to compression tests using an Instron testing machine equipped with a 1 kN load cell at a crosshead speed of 0.1 mm·min$^{-1}$. In this test, a cylindrical porous commercial bone substitute material (SKELITE™) was used as control (5 mm diameter×5 mm high).

The compressive strength is calculated according to the following formula:

$$\sigma = \frac{F}{A}$$

σ is the compressive strength
F is the force exerted on an object under compression;
A is the actual cross-sectional area through which the force is applied;
Where, $$A = \frac{A_0 L_0}{L_0 - \Delta L}$$

$A_0$ is the original specimen area of the object
$\Delta L$ is the amount by which the length of the object changes;
$L_0$ is the original length of the object.

TABLE 3

Mechanical characteristics of calcified tissue substitutes manufactured according to example 2.

| Calcified tissue substitute | Peak load (Mean ± SD) | Compressive strength (Mean ± SD) |
|---|---|---|
| A, 30% nacre | 501.06 ± 17.39 N | 6.19 ± 0.32 MPa |
| B, 35% nacre | 657.73 ± 13.65 N | 8.12 ± 0.26 MPa |
| C, 40% nacre | 820.64 ± 15.82 N | 10.12 ± 0.39 MPa |
| D, 45% nacre | 574.28 ± 27.75 N | 7.08 ± 0.54 MPa |
| E, 50% nacre | 354.34 ± 6.29 N | 4.37 ± 0.18 MPa |
| Commercial product | 44.36 ± 24.43 N | 2.26 ± 1.24 MPa |

The compressive strength of the nacre-orthophosphate particles, i.e. the calcified tissue substitutes, is 2-3 times that of the commercial product. Therefore, the calcified tissue substitutes provide stronger mechanical support in calcified tissue defects.

iii. Scanning Electron Microscopy (SEM)

Scanning electron microscopy (SEM) in back scattered electron (BSE) and secondary electron (SE) mode was used to analyse the microstructure and morphology of the five calcified tissue substitutes.

Figure 3:
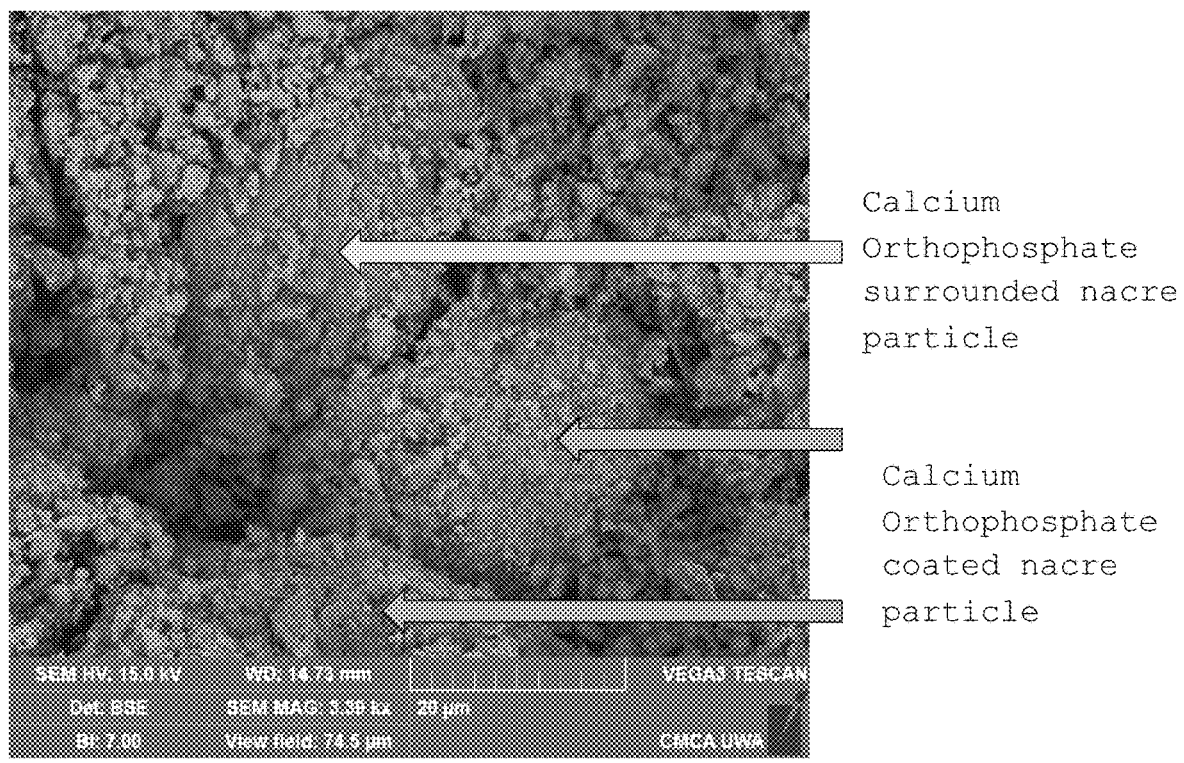
FIG. 3 is a scanning electron microscopy (SEM) micrograph collected in BSE mode with 3.39k× magnification depicting the surface of a calcified tissue substitute (nacre-orthophosphate particles) prepared according to the examples. The lighter grey arrow points to a calcium orthophosphate surrounded nacre particle and the darker grey arrows point to calcium orthophosphate coated nacre particles, which difference offers different resorption rates and aids the gradual generation of pores in the calcified tissue substitute.
Figure 4:
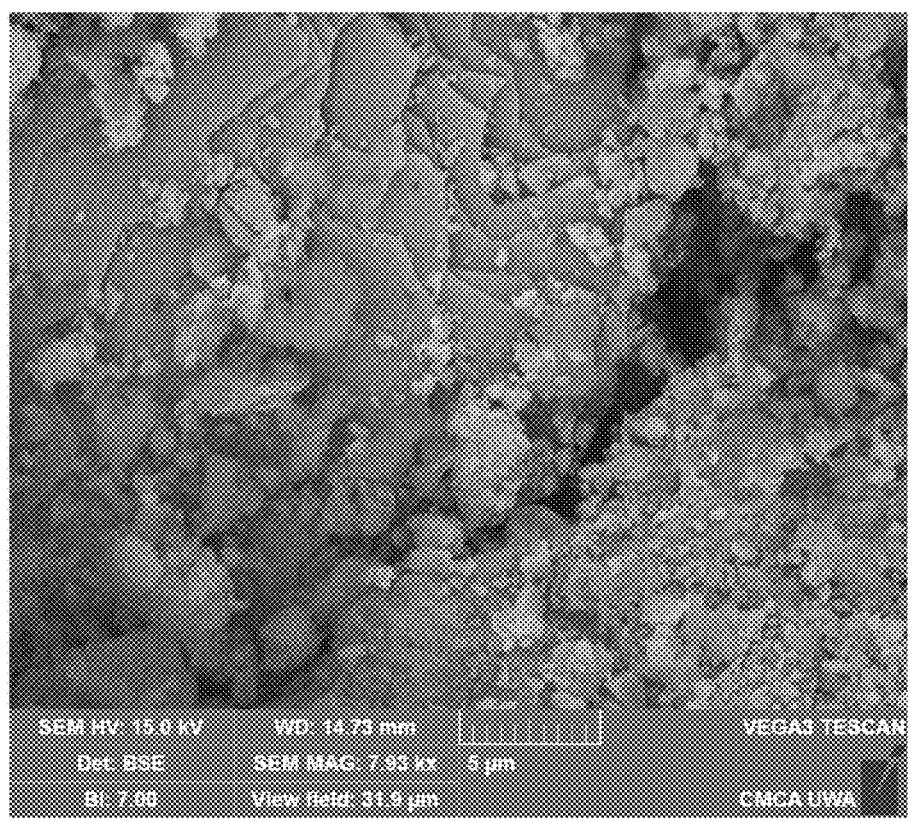
FIG. 4 is a SEM micrograph collected in BSE mode with 7.39k× magnification depicting the surface of a calcified tissue substitute (nacre-orthophosphate particles) prepared according to the examples. The micrograph shows a calcium orthophosphate surrounded nacre particle. Unreacted nacre structure can be observed.

The SEM micrographs of FIGS. 3 and 4 clearly demonstrate the surface morphology of the nacre-orthophosphate particles, i.e. the calcified tissue substitute, and show a calcium orthophosphate surrounded nacre particle and a calcium orthophosphate coated nacre particle in which the unreacted nacre provides a bioactive composition to enhance osteoinductivity and the exposed nacre has a fast resorption rate, which allows generation of pores a few weeks after implantation in body. The pores promote formation of new calcified tissue—at the early stage, the calcium orthophosphate provides mechanical support, but will be replaced by calcified tissue at a later stage.

iv. Setting Time

Initial and final setting times (tables 4 and 5) were determined by the Vicat method, which is a standard test method for time of setting of hydraulic cement paste by Vicat needles. The initial setting time is calculated as the time elapsed between the start of the reaction and the time when the needle penetration is 25 mm. The final setting time is calculated as the time elapsed when the needle does not penetrate the test material. The measurements were collected in triplicate and expressed as means±SD. (n=5)

TABLE 4

Setting times of calcified tissue substitutes manufactured according to example 2 (using nacre particles (particle size < 200 μm), brushite particles (particle size <200 μm) and tetracalcium phosphate particles (particle size <70 μm)).

| Calcified tissue substitute | Initial setting time ($T_i$, min) | Final setting time ($T_f$, min) |
|---|---|---|
| A, 30% nacre | 38.5 ± 1.2 | 60.5 ± 0.5 |
| B, 35% nacre | 55.0 ± 0.5 | 74.0 ± 0.5 |
| C, 40% nacre | 59.5 ± 0.8 | 77.0 ± 0.8 |
| D, 45% nacre | 78.3 ± 1.5 | 95.5 ± 1.5 |
| E, 50% nacre | 89.8 ± 1.2 | 114.5 ± 2.3 |

TABLE 5

Setting times of calcified tissue substitutes manufactured according to example 2 (using nacre particles (particle size<200 μm), re-ground brushite particles (particle size <30 μm) and tetracalcium phosphate particles (particle size 2-20 μm)).

| Calcified tissue substitute | Initial setting time ($T_i$, min) | Final setting time ($T_f$, min) |
|---|---|---|
| A, 30% nacre | 29.5 ± 1.0 | 46.0 ± 0.5 |
| B, 35% nacre | 41.5 ± 0.8 | 62.0 ± 0.5 |
| C, 40% nacre | 49.5 ± 1.8 | 70.0 ± 1.5 |
| D, 45% nacre | 64.3 ± 1.5 | 82.5 ± 0.5 |
| E, 50% nacre | 82.4 ± 2.2 | 107.5 ± 1.0 |

Tables 4 and 5 reveal that the setting time of the calcified tissue substitutes manufactured using finer particles as raw material is quicker than using coarser particles. Therefore, the particle size is critical for the setting time of calcified tissue substitutes.

3. In Vitro Tests

To investigate cytocompatibility of the calcified tissue substitutes, HeLa, MLO-Y4 and MC3T3 cell lines were cultured on the calcified tissue substitutes (FIGS. 5 to 8). Cell adhesion was observed by laser confocal scanning microscopy. Cell proliferation was tested by the colorimetric MTS method using hydroxyapatite as control.

v. Laser Scanning Confocal Microscopy—Cell Adhesion and Cytocopatibility a. HeLa Cell Line (24 h)

Figure 5:
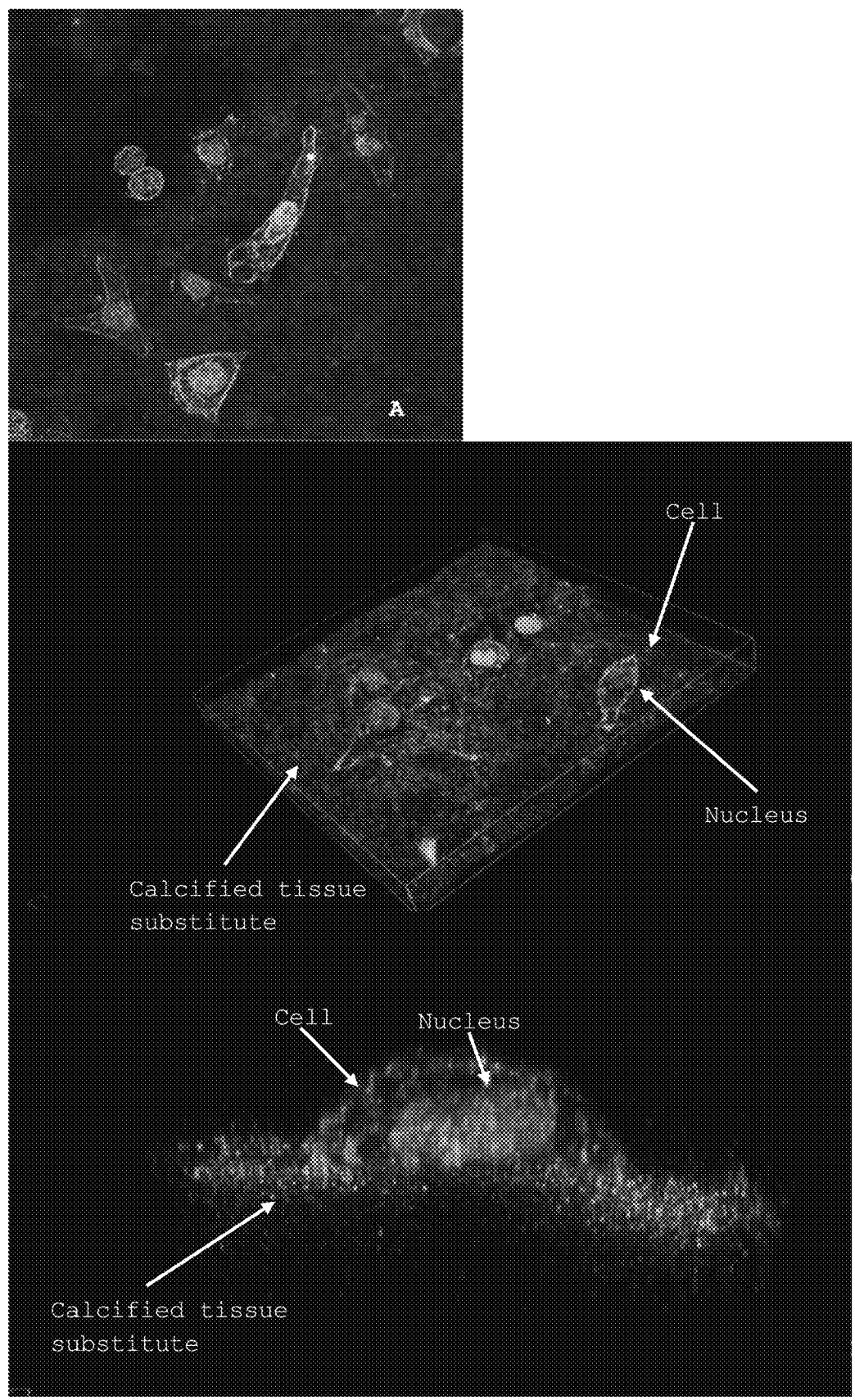
FIG. 5 comprises laser confocal scanning microscope micrographs of HeLa cells cultured for 24 hours on the calcified tissue substitute A prepared according to example 2 using nacre particles, brushite particles and tetracalcium phosphate in the ratio 6:9:5 (turquoise). F-actin in cell membranes was labelled with fluorescent phalloidin (red) and nuclei were labelled with Hoechst (blue). A. Surface morphology of the cells. B. 3D structure of the cells' adhesion to the calcified tissue substitute, with white arrows identifying a cell, a nucleus and the calcified tissue substitute. C. Elevation of a single cell adhered to the calcified tissue substitute, with white arrows identifying the cell, the nucleus and the calcified tissue substitute.

HeLa cell culture shown in FIG. 5 demonstrated good cell adhesion and cytocompatibility of the nacre-orthophosphate particles, i.e. the calcified tissue substitute.

b. MLO-Y4 Cell Line (72 h)

Figure 6:
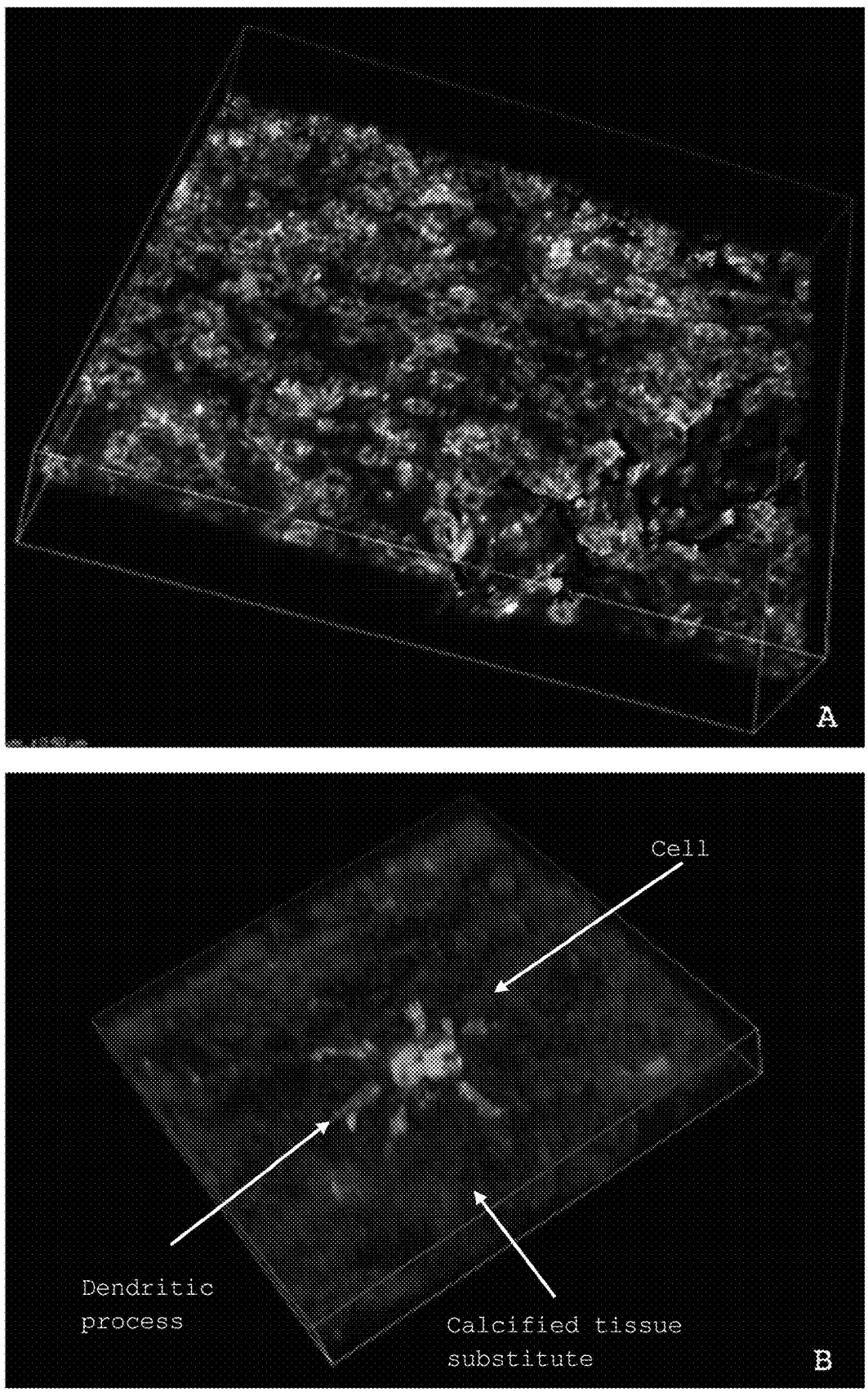

MLO-Y4 is an osteocyte-like cell line. MLO-Y4 cells cultured for 72 hours on the calcified tissue substitute A prepared according to example 2 using nacre particles, brushite particles and tetracalcium phosphate in the ratio 6:9:5. F-actin in cell membranes was labelled with fluorescent phalloidin (red). Laser confocal scanning microscopy showed the 3D structure of the cells' adhesion to the calcified tissue substitute (turquoise) and ingress into the calcified tissue substitute. FIGS. 6 and 7 show adhesion to the calcified tissue substitute (FIG. 6), growth of dendritic processes (FIG. 6B), and generation of dendritic connections (FIG. 7).

c. MC3T3 Cell Line (Up to 72 h)

MC3T3 is an osteoblast precursor cell line and was used for cell proliferation assays up to 72 h of culture. The result of the cell proliferation assay is shown in FIG. 8, in which the negative control is the absorbance of the reagent without the cells and the positive control is MC3T3 cells cultured on hydroxyapatite (Sigma-Aldrich) a common bone substitute. As shown in FIG. 8, compared with hydroxyapatite, cell proliferation was more rapid when cells were cultured on nacre-calcium orthophosphate particles, i.e. calcified tissue substitute material. The result of the cell osteogenic differentiation is shown in FIG. 9, which shows ALP activity on the nacre-calcium orthophosphate composite was significantly higher than on hydroxyapatite. This result indicated that, compared with hydroxyapatite, the nacre-calcium orthophosphate materials offered a stronger osteoinductivity for osteoblasts.

4. Animal Studies

To investigate biodegradation efficiency of the calcified tissue substitutes, cylindrical calcified tissue substitutes were implanted under the superficial fascia of the back of a rabbit. And, to investigate biocompatibility and osteoinductivity of the calcified tissue substitutes, the calcified tissue substitutes were implanted into an artificial bone defect site on the distal metaphysis region of rabbit femurs. Calcified tissue substitute C prepared according to example 2 was used in the animal studies, and hydroxyapatite was used as control.

Skeletally mature New Zealand white rabbits weighing 2.8±0.3 kg were used in the animal studies. Animals were allowed to acclimatize for 1 week before starting the experiment. They were kept separately in smooth-walled stainless-steel cages, one animal per cage, with food and water and handled in accordance with National Health and Medical Research Council (NHMRC) animal care guidelines. Morbidity, moribundity and general health observation (cage side) was performed once daily.

vi. Biodegradation Efficiency

New Zealand white rabbits were anesthetized by ear vein intravenous injection of Amylobarbitone (0.03 mg/kg of body weight). The cylindrical materials (10 mm in diameter, 5 mm in height, four nacre-calcium orthophosphate materials and four hydroxyapatite materials) were implanted under the animals' bilateral paravertebral superficial fascia through a dorsal midline approach (nacre-calcium orthophosphate materials in the left, hydroxyapatite materials in the right). One of each material was removed at four different time points (3 weeks, 6 weeks, 9 weeks or 12 weeks), weighed, and the percentage weight loss of each calculated. The test was performed in triplicate, and the mean±SD of weight loss percentages in each time course calculated. FIG. 10A is a line chart showing biodegradation rate and FIG. 10B comprises photographs showing morphology of degraded materials over the time course. The line chart of FIG. 10A shows that the biodegradation rate of the nacre-calcium orthophosphate material was significantly faster than that of hydroxyapatite. However, as shown in FIG. 10B for the nacre-calcium orthophosphate material, although an eroded surface of the material was observed, the cylindrical shape was maintained. This indicates that the biodegradation of the calcified tissue substitutes was quicker than hydroxyapatite, the most commonly used bone substitute biomaterial. And the biodegradation rate was gradual and moderate, without the collapse of physical support.

vii. Biocompatibility and Osteoconductivity

New Zealand white rabbits were anesthetized by ear vein intravenous injection of Amylobarbitone (0.03 mg/kg of body weight). The animals were placed supine on the operating table and the experimental knee (right) shaved, prepared, and draped in a sterile fashion. The metaphysis region in right femur was entered by a longitudinal medial parapatellar incision and the patella was dislocated laterally to expose the femoral cortical bone. A circular defect, 5 mm in diameter, 5 mm in depth, 2.5 mm away from lineae epiphysialis of the femur, was created with a stainless steel dental drill. Then, the different calcified tissue substitutes (nacre-orthophosphate) or control material (hydroxyapatite) were implanted into different bone defect sites according to table 5. The incision was closed layer by layer. Each rabbit had only one femur operated on, and a total of 33 defects were created in 33 rabbits (FIG. 11). Postoperatively, the animal model was confirmed by X-ray and Micro-CT of the Surgery Control group (FIG. 12). Afterward, the rabbits were returned to their cages and allowed to ambulate freely. In the first 3 days after surgery, an anti-infective treatment was given to each rabbit through an intramuscular injection of Cefazolin (200 mg/kg).

After 4 weeks and 8 weeks, all rabbits were sacrificed, the right femurs retrieved, and the soft tissues removed (FIG. 13). Then, the samples were dehydrated in an ethanol gradient at ethanol/water volume fractions before going through the Micro-CT scan and assay.

TABLE 5

Biocompatibility and osteoinductivity animal study.

| Group | Bone substitute material | Sacrifice time point | Sample |
|---|---|---|---|
| NO4 | Nacre-calcium orthophosphate | 4 weeks | n = 5 |
| NO8 | Nacre-calcium orthophosphate | 8 weeks | n = 5 |
| HA4 | Hydroxyapatite | 4 weeks | n = 5 |
| HA8 | Hydroxyapatite | 8 weeks | n = 5 |
| BC4 | No implant (Blank control) | 4 weeks | n = 5 |
| BC8 | No implant (Blank control) | 8 weeks | n = 5 |
| Surgery control | No implant | After surgery | n = 3 |

The retrieved femurs were scanned and reconstructed at high resolution using a micro-CT to observe the bone/implant interface (FIG. 14 A, B, C, D, E, F). The specimens were scanned with μCT (Skyscan1172, Bruker, Germany) at 70 keV and 145 μA with an isotropic resolution of 10.5 μm in all three dimensions. The entire femur was scanned. For each scan, the scanning was performed at the distal femur and continued proximally 0.5 mm. The total volume of selected regions was constant (48 mm$^3$). Grey thresholds applied to 3D images were used to separate the newly formed bone tissues (threshold 60) from residual materials (threshold 110). The volume of newly formed bone tissues at the defect site was calculated by subtracting threshold 60 from threshold 110. The volume fraction of new bone tissues was expressed as a percentage of the selected volume. The degradation rate was determined by calculating difference of the volume fraction of materials at various implantation times. Three replicates were performed for each sample. After that, the values of Bone Volume/Total Volume (BV/TV), Bone Surface/Bone Volume (BS/BV), Cortical Thickness (Ct.Th), Fractal dimension (FD) and the Percent porosity (PoV/TV %) were calculated (FIGS. 15, 16, 17).

From observation of the retrieved samples by naked eyes (FIG. 13) and the image of Micro-CT (FIGS. 14A and 14D), there was no sign of inflammation, infection or rejection, such as inflammatory exudation from bone defect site, osteolysis, bone destruction, etc. From the general health observation of the animals, the rabbits were generally healthy after surgery, no obvious infective and allergic signs were detected. Thus, the study indicated that the nacre-calcium orthophosphate material is a safe and biocompatible implant.

From the images of Micro-CT, after 4 weeks and 8 weeks, the surrounding bone tissue tightly connected with the nacre-calcium orthophosphate material, which indicated good osteointegration of the material (FIGS. 14A and 14D). Compared with the blank control group (FIGS. 14C and 14F), both implanted nacre-calcium orthophosphate and hydroxyapatite promoted recovery of the bone defect. However, in 8 weeks, the nacre-calcium orthophosphate-implanted group showed better continuity of the cortical bone on the bone defect side than the hydroxyapatite-implanted group (FIGS. 14D and 14E), which indicated better bone-healing properties. More importantly, the cortical bone thickness of the nacre-calcium orthophosphate-implanted group is clearly thicker than that of the hydroxyapatite-implanted group, which indicated a stronger periosteal reaction. Precisely, it indicated potent osteoblast activity stimulated by the calcified tissue substitutes.

As shown in the results of Micro-CT data analysis (FIGS. 15, 16, 17), the BV/TV and BS/BV of nacre-calcium orthophosphate-implanted group were statistically higher than those of hydroxyapatite-implanted. Moreover, in 4 weeks, the porosity of the bone defect site of nacre-calcium orthophosphate-implanted group was lower than that of the hydroxyapatite-implanted group. The results indicate that a greater volume of new bone had been formed in the nacre-calcium orthophosphate-implanted group, which could be explained by the osteoinductivity of nacre-calcium orthophosphate material.

In summary, as an important part of pre-clinical tests, the animal studies confirmed that, compared with conventional calcium phosphate materials, such as hydroxyapatite, the nacre-calcium orthophosphate material was a better bone substitute, due to its quick biodegradation rate, good biocompatibility and osteoinductivity.

The invention claimed is:
1. A method for manufacturing a substitute composition for repairing a calcified tissue, the method comprising:
 (i) reacting ground nacre, monocalcium phosphate, and water to produce brushite and unreacted ground nacre, wherein said ground nacre has a particle size of 200 µm or less;
 (ii) grinding the brushite to produce ground brushite with a particle size of 30 µm or less;
 (iii) reacting ground nacre with the ground brushite and tetracalcium phosphate with a particle size of 2 µm to 20 µm in disodium hydrogen phosphate solution to form said substitute composition, which substitute composition comprises unreacted nacre, unreacted brushite, and carbonate apatite;
 wherein said substitute composition has a final setting time ($T_f$) of between 60 min to 120 min.
2. The method of claim 1, wherein the ground nacre and monocalcium phosphate are reacted in a ground nacre to monocalcium phosphate weight-to-weight ratio of 4:10.
3. The method claim 1, wherein the disodium hydrogen phosphate solution has a pH of 8.2 to 9.5.
4. The method claim 1, wherein the disodium hydrogen phosphate solution is a 2.5% to 4% solution.
5. The method of claim 1, wherein the ground nacre and monocalcium phosphate are reacted at room temperature or at about 37° C. and/or the ground nacre and ground brushite are reacted at room temperature or at about 37° C.
6. The method of claim 1, further comprising drying the brushite before grinding the brushite.
7. The method of claim 1, further comprising separating the ground brushite so that all of the particles of ground brushite have a particle size of 10 µm to 30 µm.
8. The method of claim 1, wherein the ground nacre and ground brushite are reacted in a ground nacre to ground brushite weight-to-weight ratio of 4:10.
9. The method of claim 1, wherein the ground nacre, ground brushite, and tetracalcium phosphate are reacted in a ground nacre to ground brushite to tetracalcium phosphate weight-to-weight ratio of 6:9:5, 7:8:5, 8:7:5, 9:6:5, or 10:5:5 in disodium hydrogen-phosphate solution.
10. The method of claim 1, wherein disodium hydrogen phosphate solution is reacted with other reactants in a solution:reactant ratio of 25%, 33%, 40% or 50%.
11. The method of claim 1, further comprising adding an agent selected from the group consisting of hectorite, laponite and alpha-calcium sulphate.
12. The method of claim 1 wherein the substitute composition is set at 100% humidity and 37° C.
13. The method of claim 1 wherein the substitute composition has a peak load of greater than 45 N or a compressive strength of greater than 2.3 MPa.
14. The method of claim 1 wherein the substitute composition is implantable or injectable.
15. The method of claim 1 wherein the substitute composition has an initial setting time ($T_i$) of 30 min to 90 min.

* * * * *